US012630649B2

(12) United States Patent
Balthasar et al.

(10) Patent No.: US 12,630,649 B2
(45) Date of Patent: May 19, 2026

(54) COMPOSITIONS AND METHODS FOR IMPROVING TUMOR PENETRATION OF TUMOR SPECIFIC ANTIBODIES

(71) Applicant: The Research Foundation for The State University of New York, Amherst, NY (US)

(72) Inventors: Joseph P. Balthasar, Lancaster, NY (US); Brandon M. Bordeau, Amherst, NY (US)

(73) Assignee: The Research Foundation for The State University of New York, Amherst, NY (US)

( * ) Notice: Subject to any disclaimer, the term of this patent is extended or adjusted under 35 U.S.C. 154(b) by 1093 days.

(21) Appl. No.: 17/640,760

(22) PCT Filed: Sep. 10, 2020

(86) PCT No.: PCT/US2020/050159
§ 371 (c)(1),
(2) Date: Mar. 4, 2022

(87) PCT Pub. No.: WO2021/050696
PCT Pub. Date: Mar. 18, 2021

(65) Prior Publication Data
US 2022/0315670 A1 Oct. 6, 2022

Related U.S. Application Data

(60) Provisional application No. 62/898,445, filed on Sep. 10, 2019.

(51) Int. Cl.
| | |
|---|---|
| *A61K 47/02* | (2006.01) |
| *A61K 9/00* | (2006.01) |
| *A61K 47/68* | (2017.01) |
| *C07K 16/32* | (2006.01) |
| *C07K 16/42* | (2006.01) |

(52) U.S. Cl.
CPC ........ *C07K 16/4208* (2013.01); *A61K 9/0019* (2013.01); *A61K 47/02* (2013.01); *A61K 47/68033* (2023.08); *A61K 47/6863* (2017.08); *C07K 16/32* (2013.01)

(58) Field of Classification Search
CPC .......... C07K 16/4208; C07K 2317/569; C07K 2317/76; A61K 9/0019; A61K 47/68033; A61K 47/6851; A61K 2039/505; A61K 2039/507; A61K 39/395
USPC ...................................................... 424/143.1
See application file for complete search history.

(56) References Cited

U.S. PATENT DOCUMENTS

| | | | |
|---|---|---|---|
| 6,042,827 | A | 3/2000 | Baldwin et al. |
| 9,556,273 | B2 | 1/2017 | Van Ginderachter et al. |
| 2015/0093336 | A1 | 4/2015 | Van Ginderachter et al. |
| 2015/0204879 | A1 | 7/2015 | Pohlmann et al. |

FOREIGN PATENT DOCUMENTS

| | | |
|---|---|---|
| WO | 2005/061546 A1 | 7/2005 |
| WO | 2006/116423 A2 | 11/2006 |
| WO | 2008031126 A1 | 3/2008 |
| WO | 2009/003082 A2 | 12/2008 |
| WO | 2010130677 A1 | 11/2010 |
| WO | 2016124781 A1 | 8/2016 |

OTHER PUBLICATIONS

Harmsen and Haard (Appl Microbiol Biotechnol 2007, 77:13-22).*
Alvarez-Rueda, N., et al., A llama single domain anti-idiotypic antibody mimicking HER2 as a vaccine: Immunogenicity and efficacy, Vaccine, Jun. 11, 2009, vol. 27, pp. 4826-4833.
Coelho, M., et al., Isolation and characterisation of a human anti-idiotypic scFv used as a surrogate tumour antigen to elicit an anti-HER-2/neu humoral response in mice, British Journal of Cancer, Apr. 27, 2004, vol. 90, pp. 2032-2041.
Mohanty, K., et al., Anti-tumor immunity induced by an anti-idiotype antibody mimicking human Her-2/neu, Breast Cancer Research and Treatment, Sep. 27, 2006, vol. 104, pp. 1-11.
Pal, S., et al., Generation of Her-2/neu Vaccine Utilizing Idiotypic Network Cascade, Cancer Biology & Therapy, Dec. 2007, vol. 6, No. 12, pp. 1916-1925.

* cited by examiner

*Primary Examiner* — Yan Xiao
(74) *Attorney, Agent, or Firm* — Hodgson Russ LLP

(57) ABSTRACT

Provided are compositions and methods for improving tumor penetrability of anti-tumor antibodies or conjugates thereof. The method comprises administering to an individual in need of treatment an anti-idiotypic antibody in addition to the anti-tumor antibody or conjugate. Examples are provided for anti-HER2 antibodies and anti-idiotypic antibodies that are directed to the anti-HER2 antibodies.

8 Claims, 13 Drawing Sheets

Specification includes a Sequence Listing.

A.

| Name | $k_a$ | $k_d$ | $K_D$ |
|------|-------|-------|-------|
| 1HE | 2.162(3)e5 | 7.236(7)e-6 | 33.47(6)pM |

B.

| | AUClast (day*nM) | AUClast (1HE) | P-value | CI (L/daykg) | CI (1HE) | P-value |
|---|---|---|---|---|---|---|
| 0.1 mg/kg (SD) | 33.18 (5.071) | 26.83 (3.96) | 0.058 | 0.0089 (0.0031) | 0.122 (0.0028) | 0.116 |
| 1 mg/kg (SD) | 302.9 (37.45) | 295.6 (98.89) | 0.881 | 0.0011 (0.00015) | 0.0011 (0.00045) | 0.885 |
| 10 mg/kg (SD) | 3077 (121.2) | 3133 (239.7) | 0.655 | 9.8E-5 (1.05E-5) | 0.0001 (1.89E-5) | 0.635 |

| Mutant | Point Mutation | $T_{1/2}$ |
|--------|----------------|-----------|
| 1D6 | D56N | 3.9 |
| 1C5 | L11M, F29L, V32A, K76R, Y111H | 4.2 |
| 1F3 | D56Y | 5.1 |
| 2H2 | G9D, T28A | 5.4 |
| 1E8 | S57G | 6.0 |
| 1C12 | Deletion E1-A33, F37Y | 6.0 |
| 2D11 | K76R | 8.8 |
| 1G1 | N54D, D56G | 12.1 |
| 1C3 | A97V | 12.1 |
| 2G2 | Y111N | 12.8 |
| 1HE |  | 17.4 |
| 1G11 | G10D, S31G, D56V | 35.1 |
| 2F9 | D105E | 55.5 |
| 2A10 | Deletion E1-A33, T103A | 56.5 |
| 2C4 | T103A, Q117L | 84.1 |
| 2D7 | T103A | 105.3 |
| 2A4 | T58A | 186.7 |
| 2E10 | L18Q, T103A | 481.6 |

Figure 13B

SEQUENCE LISTING

```
<160> NUMBER OF SEQ ID NOS: 8

<210> SEQ ID NO 1
<211> LENGTH: 130
<212> TYPE: PRT
<213> ORGANISM: Artificial Sequence
<220> FEATURE:
<223> OTHER INFORMATION: 1HE

<400> SEQUENCE: 1

Glu Val Gln Leu Val Glu Ser Gly Gly Gly Leu Val Gln Ala Gly Asp
1               5                   10                  15

Ser Leu Thr Leu Ser Cys Ala Ala Ser Gly Arg Thr Phe Ser Ser Val
            20                  25                  30

Ala Met Gly Trp Phe Arg Gln Ala Pro Gly Lys Glu Arg Lys Phe Val
        35                  40                  45

Ala Asn Ile Ser Trp Asn Gly Asp Ser Thr Tyr Tyr Thr Asp Ser Val
    50                  55                  60

Lys Gly Arg Phe Thr Ile Ser Arg Asp Asn Ala Lys Asn Thr Val Tyr
65                  70                  75                  80

Leu Gln Met Ser Ser Leu Lys Pro Glu Asp Thr Ala Val Tyr Tyr Cys
            85                  90                  95

Ala Ala Asp Val Arg Trp Thr Gly Asp Gly His Arg Ala Asp Tyr Trp
            100                 105                 110

Gly Gln Gly Thr Gln Val Thr Val Ser Ser Leu Glu His His His His
        115                 120                 125

His His
    130
```

```
<210> SEQ ID NO 2
<211> LENGTH: 122
<212> TYPE: PRT
<213> ORGANISM: Artificial Sequence
<220> FEATURE:
<223> OTHER INFORMATION: 1HE without restriction site amino acids and
      hexahistidine tag

<400> SEQUENCE: 2

Glu Val Gln Leu Val Glu Ser Gly Gly Gly Leu Val Gln Ala Gly Asp
1               5                   10                  15

Ser Leu Thr Leu Ser Cys Ala Ala Ser Gly Arg Thr Phe Ser Ser Val
            20                  25                  30

Ala Met Gly Trp Phe Arg Gln Ala Pro Gly Lys Glu Arg Lys Phe Val
            35                  40                  45

Ala Asn Ile Ser Trp Asn Gly Asp Ser Thr Tyr Tyr Thr Asp Ser Val
    50                  55                  60

Lys Gly Arg Phe Thr Ile Ser Arg Asp Asn Ala Lys Asn Thr Val Tyr
65                  70                  75                  80

Leu Gln Met Ser Ser Leu Lys Pro Glu Asp Thr Ala Val Tyr Tyr Cys
                85                  90                  95

Ala Ala Asp Val Arg Trp Thr Gly Asp Gly His Arg Ala Asp Tyr Trp
            100                 105                 110

Gly Gln Gly Thr Gln Val Thr Val Ser Ser
        115                 120

<210> SEQ ID NO 3
<211> LENGTH: 378
<212> TYPE: DNA
<213> ORGANISM: Artificial Sequence
<220> FEATURE:
<223> OTHER INFORMATION: 1HE genetic sequence

<400> SEQUENCE: 3
catatggaag ttcagctggt tgaaagcggt ggtggtctgg ttcaggcagg cgatagtctg       60
accctgagct gtgcagcaag cggtcgtacc tttagcagcg ttgcaatggg ttggtttcgt      120
caggcaccgg gtaaagaacg taaatttgtt gcaaatatta ctggaatgg cgacagcacc       180 tattataccg atagcgttaa aggtcgtttt accattagcc gtgataatgc caaaaatacc      240
gtttacctgc agatgagcag cctgaaaccg gaagataccg cagtgtatta ttgtgcagca      300
gatgttcgtt ggaccggtga tggtcatcgt gcagattatt ggggtcaggg cacccaggtt      360
accgttagca gcctcgag                                                    378

<210> SEQ ID NO 4
<211> LENGTH: 5
<212> TYPE: PRT
<213> ORGANISM: Artificial Sequence
<220> FEATURE:
<223> OTHER INFORMATION: 1HE CDR2 center sequence

<400> SEQUENCE: 4

Asn Gly Asp Ser Thr
1               5

<210> SEQ ID NO 5
<211> LENGTH: 9
<212> TYPE: PRT
<213> ORGANISM: Artificial Sequence
<220> FEATURE:
<223> OTHER INFORMATION: CDR3 sequence
```

-continued

```
<400> SEQUENCE: 5

Thr Gly Asp Gly His Arg Ala Asp Tyr
1               5

<210> SEQ ID NO 6
<211> LENGTH: 8
<212> TYPE: PRT
<213> ORGANISM: Artificial Sequence
<220> FEATURE:
<223> OTHER INFORMATION: CDR1

<400> SEQUENCE: 6

Gly Arg Thr Phe Ser Ser Val Ala
1               5

<210> SEQ ID NO 7
<211> LENGTH: 11
<212> TYPE: PRT
<213> ORGANISM: Artificial Sequence
<220> FEATURE:
<223> OTHER INFORMATION: CDR2

<400> SEQUENCE: 7

Ile Ser Trp Asn Gly Asp Ser Thr Tyr Tyr Thr
1               5                   10

<210> SEQ ID NO 8
<211> LENGTH: 15
<212> TYPE: PRT
<213> ORGANISM: Artificial Sequence
<220> FEATURE:
<223> OTHER INFORMATION: CDR3

<400> SEQUENCE: 8

Ala Ala Asp Val Arg Trp Thr Gly Asp Gly His Arg Ala Asp Tyr
1               5                   10                  15
```

COMPOSITIONS AND METHODS FOR IMPROVING TUMOR PENETRATION OF TUMOR SPECIFIC ANTIBODIES

CROSS-REFERENCE TO RELATED APPLICATIONS

This application claims priority to U.S. Provisional patent application no. 62/898,445, filed on Sep. 10, 2019, the disclosure of which is incorporated herein by reference.

BACKGROUND OF THE DISCLOSURE

Targeted anti-cancer therapeutics such as monoclonal antibodies and antibody-cytotoxin conjugates have shown dramatic growth over the past decade. Several antibodies have received FDA approval for oncology indications, with several more in late-stage clinical development. Despite the continued growth of antibody therapy, it is recognized that antibody uptake and penetration in solid tumors is poor, leading to suboptimal efficacy. It is considered that physical barriers present within solid tumors may impede uptake and penetration of the therapeutic antibodies, thereby limiting efficacy. Poor disposition of antibody in tumors may be caused by many factors. For example, it has been observed that a majority of antibody present within a solid tumor is bound to cancer cells in the peri-vascular region (Dennis et al., Cancer Res, 2007. 67(1): p. 254-6; Lee et. A; BMC Cancer, 2010. 10: p. 255). Penetration of high-affinity antibodies is limited by successful binding of antibody to cellular antigen at the point of extravasation, leading to sequestration of antibody and sub-optimal tumor exposure (Juweid et al., Cancer Research, 1992. 52(19): p. 5144-5153; Rudnick et al., Cancer Biother Radiopharm, 2009. 24(2): p. 155-61; Fujimori et al. J Nucl Med, 1990. 31(7): p. 1191-8). This phenomenon is termed as the binding site barrier (BSB). Prior methods to overcome BSB include the use of low-affinity antibodies (Adams et al., Cancer Res, 2001. 61(12): p. 4750-5; Rudnick et al., Cancer Res, 2011. 71(6): p. 2250-9; Kievit et al., Br J Cancer, 1996. 73(4): p. 457-64), antibody fragments (Schmidt et al., Mol Cancer Ther, 2009. 8(10): p. 2861-71) and high antibody doses (Lee et al., BMC Cancer, 2010. 10: p. 255; Rhoden et al., J Pharm Sci, 2012. 101(2): p. 860-7), with each approach having unacceptable caveats. Low-affinity antibodies and antibody fragments have poor tumor selectivity and uptake (Adams et al., Cancer Res, 1998. 58(3): p. 485-90), whereas, saturation of tumor antigen with high doses can require several grams of antibody per patient (Thurber et al., Mol Imaging Biol, 2011. 13(4): p. 623-32), leading to feasibility issues with administration and an increased risk of off-target toxicities (Ascierto et al., Annals of Oncology, 2016. 27(suppl 6): p. 11060-11060; McDermott et al., Journal of Clinical Oncology, 2015. 33(18): p. 2013-2020; Younes et al., J Clin Oncol, 2012. 30(22): p. 2776-82; Watanabe et al., Cancer Sci, 2005. 96(12): p. 903-10). As such, there is continued need in the area of solid tumor therapeutics to improve antibody distribution within the tumor and therefore, and thereby, its efficacy.

SUMMARY OF THE DISCLOSURE

This disclosure provides compositions and methods for improving distribution of tumor-specific antibodies within a tumor. The present compositions and methods provide a strategy to overcome the binding site barrier through transient competitive inhibition of antibody-antigen binding. It was surprising that transient competitive inhibition of tumor-specific antibodies resulted in increased penetration and increased tumor growth inhibition.

In an aspect, this disclosure provides compositions for improving penetration of anti-tumor antibodies within a tumor. In an embodiment, the composition comprises i) an anti-tumor antigen antibody (or an antigen binding fragment or derivative thereof), and ii) an anti-idiotypic antibody (or an antigen binding fragment thereof), which is specific for the anti-tumor antibody (or its fragments or derivatives). The idiotype in an anti-idiotypic antibody is the CDR regions or the antigen binding determinant of an antibody. In an embodiment, the anti-idiotypic antibody is a single domain antibody (nanobody). The anti-tumor antibody (or a fragment or derivative thereof) and the anti-idiotypic antibody (or a fragment/derivative thereof) may be provided in the same composition or in separate compositions, the same number of administrations or different number of administrations.

In an aspect, this disclosure provides a method for inhibiting or preventing the growth of tumor comprising administering to an individual in need of treatment, an anti-tumor antigen antibody, and an anti-idiotypic antibody directed to the anti-tumor antigen antibody. In an embodiment, the disclosure provides a method for improving penetration of anti-tumor antibodies in a tumor comprising administering to an individual in need of treatment the anti-tumor antibody and an anti-idiotypic antibody directed to the anti-tumor antibody. The anti-tumor antibody and the anti-idiotypic antibody may be administered in the same composition or in separate compositions. The administrations are such that the anti-tumor antibody and the inhibitor (e.g., anti-idiotypic antibody) interact at the tumor site and exhibit transient competitive binding.

To demonstrate the efficacy of the present strategy, trastuzumab (Herceptin), which is an anti-tumor antibody directed to HER2, and an anti-idiotypic single domain antibody against trastuzumab, 1HE, was used. SKOV3 tumors obtained from mice administered trastuzumab alone and in combination with 1HE were fluorescently stained and imaged to assess trastuzumab distribution. 1HE significantly improved tumor penetration of trastuzumab. Further, co-administration of 1HE with ado-trastuzumab emtansine (T-DM1) in NCI-N87 xenograft-bearing mice led to a significant improvement in survival in comparison to T-DM1 alone with an increase in the median survival from 29 to 42 days. These results demonstrate that transient competitive inhibition improves antibody tumor distribution and as a result enhances efficacy.

DETAILED DESCRIPTION OF THE DISCLOSURE

Figure 1:
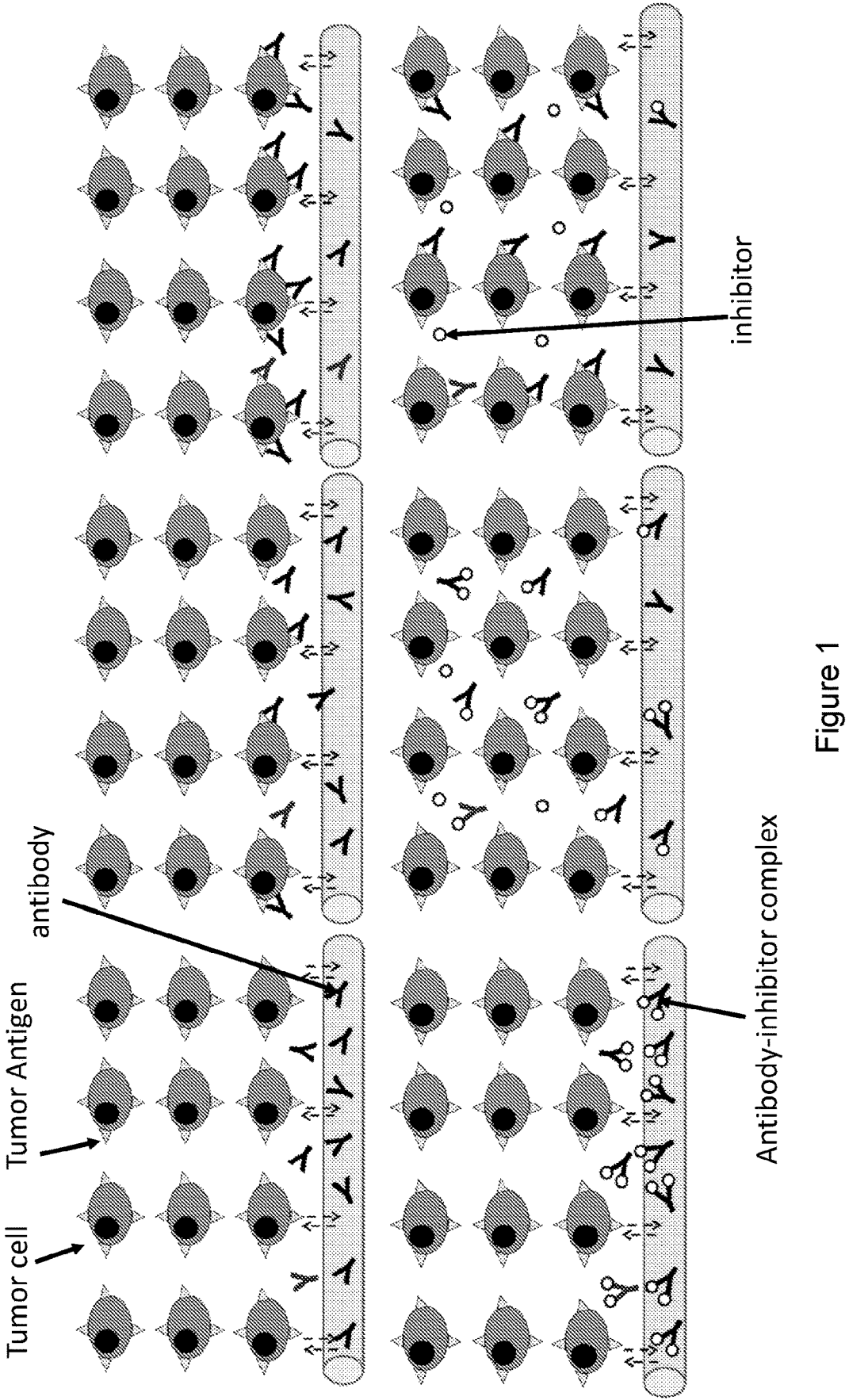
FIG. 1: Bypassing the binding site barrier: graphic representation of competitive inhibition strategy. The top panels represent the binding site barrier, with antibody that extravasates into tumor (top left) successfully binding antigen expressing cells in the perivascular region (top middle), with most tumor cells remaining untargeted (top right). The bottom panels illustrate the present competitive inhibition strategy with the antibody-inhibitor complex (e.g., [anti-tumor antibody]-[anti-idiotypic antibody] complex) extravasating into the tumor (bottom left) and diffusing throughout the interstitial space (bottom middle). Over time the antibody-inhibitor complex dissociates with free anti-tumor antibody binding antigen expressing cells at the point of dissociation, improving tumor cell targeting (bottom right). An anti-idiotypic antibody is an example of an inhibitor.

The term "treatment" as used herein refers to reduction or delay in one or more symptoms or features associated with the presence of the particular condition being treated. Treatment does not necessarily mean complete cure and does not preclude relapse. Treatment may be carried out over a short period of time (days, weeks), or over a long period of time (months) or may be on a continuous basis (e.g., in the form of a maintenance therapy). Treatment may be continual or intermittent.

The term "therapeutically effective amount" as used herein is the amount sufficient to achieve, in a single or multiple doses, the intended purpose of treatment. The exact amount desired or required will vary depending on the mode of administration, patient specifics and the like. Appropriate effective amounts can be determined by one of ordinary skill in the art (such as a clinician) with the benefit of the present disclosure.

Where a range of values is provided in this disclosure, it should be understood that each intervening value, to the tenth of the value of the lower limit between the upper and lower limit of that range, and any other intervening value in that stated range is encompassed within the disclosure, unless clearly indicated otherwise. The upper and lower limits of these smaller ranges may independently be included in the smaller ranges encompassed within the disclosure.

As used in this disclosure, the singular forms include the plural forms and vice versa unless the context clearly indicates otherwise. The indefinite articles "a" and "an" as used in the specification and claims should be understood to mean "at least one" unless clearly indicated otherwise.

A general reference to an antibody in this disclosure is also intended to include all antigen binding fragments or modifications of such antibody.

The present disclosure is based, at least in part, on the surprising observations that penetrability and distribution of anti-tumor antibodies within a tumor, and therefore growth inhibition, may be improved by providing to the tumor, anti-tumor antibodies in a state of reversible binding with anti-idiotypic antibodies. It was observed that having the anti-tumor antibodies in a reversible binding state with an anti-idiotypic antibody (or an inhibitor that interferes with the binding of the anti-tumor antibody to the tumor antigen) allows circumvention of binding site barrier phenomenon whereby most of the anti-tumor antibody is restricted to the perivascular region due to binding to the target antigen in that region.

The anti-tumor antibody (also referred to herein as anti-tumor antigen antibody) may be, and the term antibody encompasses, whole immunoglobulin molecules such as polyclonal or monoclonal antibodies or may be antigen-binding fragments thereof, including but not limited to, Fab, F(ab'), F(ab')2, Fv, dAb, Fd, CDR fragments, single-chain antibodies (scFv), bivalent single-chain antibodies, single-chain phage antibodies, diabodies, single domain antibodies (nanobodies) and the like. The fragments of the antibodies may be produced synthetically or by enzymatic or chemical cleavage of intact immunoglobulins or may be genetically engineered by recombinant DNA techniques. These techniques are well known in the art. Modifications of the antibody include one or more mutations.

The antibodies useful for the present method may be obtained from a human or a non-human animal. The antibody may be of any class (for example, IgG, IgE, IgM, IgD, IgA and IgY), or any subclass (eg., IgG1, IgG2, IgG3, IgG4, IgA1 and IgA2). In an embodiment, single domain antibodies or nanobodies produced by camelids in response to introducing APP cleavage products (or peptide fragments thereof) into the camelids can be used. The nanobodies are typically heavy chain antibodies and thus contain heavy chain homodimers and do not contain antibody light chains. These antibodies typically comprise a single variable domain and two constant domains (CH2 and CH3).

The anti-tumor antibody may be conjugated to a cytotoxin. For example, the anti-tumor antibody may be conjugated to a cytotoxic drug (e.g., antibody drug conjugate or ADC). Other antibody-cytotoxin conjugates include immunotoxin and radionuclide conjugates. The number of antigens on a single tumor cell commonly ranges from $10^5$-$10^6$, therefore, perivascular antigen saturation with potent antibody-cytotoxin conjugates leads to overkilling of saturated cells at the expense of limited therapeutic effect in hypoxic tumor regions. Similar to the impact of 1HE on T-DM1 as demonstrated here, co-administration of a competitive inhibitor can be lead to significant improvements in the efficacy of immunotoxin and radionuclide antibody conjugates.

Any antibody that is directed against a tumor antigen may be used in the present disclosure. There are several monoclonal antibodies that have been demonstrated as successful therapeutic agents for the treatment of human cancers. These include rituximab, trastuzumab, cetuximab, panitumumab, bevacizumab and many others. Examples of monoclonal antibodies indicated against solid tumors include pertuzumab, ramucirumab, nivolumab, pembrolizumab, necitumumab, dinutuximab, olaratumab, atezolizumab, avelumab, cemiplimab, carotuximab, margetuximab, bemarituzumab, naxitamab, relatlimab, BCD-100, spartalizumab, IBI308, CS1001, tremelimumab, TSR-042).

In an embodiment, antibody drug conjugates or conjugates of antibodies with immunotoxins or other cytotoxics or radionuclides may be used. An example is trastuzumab emtansine (TDM1). Other examples include Trastuzumab deruxtecan, Trastuzumab duocarmazine, sacituzumab govitecan, oportuzumab monatox, BAT8001, zolbetuximab claudiximab, depatuxizumab mafodotin, L19IL2, L19TNF, mirvetuximab sorvatansine, rovalpituzumab tesirine, enfortumab vedotin. Examples of cytotoxin conjugates that can be used for the proposed strategy include: maytansinoids, auristatins, camptothecin derivatives, pyrrolobenzodiazepines, calicheamicin, gelonin, diphtheria toxin, *Pseudomonas* exotoxin and derivatives (e.g. PE38, PE40), alpha-emitters (Ac-225, At-211, Th-227, Ra-223, Pb-212, Bi-212, Ra-224), siRNA, enzymes (carboxypeptidase, alkaline phosphatase, cytosine deaminase), immunocytokines (e.g. Interleukin-2).

Therapeutics that are specific against HER2 receptors include trastuzumab (Roche) and pertuzumab (Roche), which are humanized IgG1/k antibodies, and trastuzumab-emtansine (T-DM1) (Roche) and fam-trastuzumab-deruxte-can-nxki DS8201 (AstraZeneca) are ADCs. Trastuzumab biosimilars include Ontruzant SB3 (Samsung Bioepis), Her-zuma CT-P6 (Celltrion), Ogivri MYL-14010 (Mylan/Bio-con), Kanjinti ABP980 (Amgen), Trazimera PF-05280014 (Pfizer). Alternatives to trastuzumab include Margetuximab (MacroGenics/MSD), TrasGex Timigutuzumab (Glyco-tope), 3E10 (Laboratory of Antibody Medicine and Targeted Therapy, Shanghai, China), H2-18 (Second Military Medi-cal University, Shanghai, China), and HuA21 (Anhui Medi-cal University, Hefei, China). Alternatives to T-DM1 include SYD985 (Synthon), BAT8001 (Bio-Thera), RC48 (Reme-Gen), A166 (Kluspharma), MEDI4276 (MedImmune), DHES0815A (Genentech), ALT-P7 (Alteogen), ARX-788 (Ambrx), B003 (Shanghai Pharm.), LCB14-0110 (Le-goChem), SHR-A1201 (Jiangsu HengRui Medicine), DP303c (CSPC Pharm.), ZW49 (Zymeworks), and MT-5111 (Molecular Templates). Several new products have also been proposed including KN026 (Jiangsu Alphamab), ZW25I (Dragonfly Therapeutics), FHR4 based immunoconjugate (Luxembourg Institute of Health), ST8176AA1 (Al-fasigma).

The anti-idiotypic antibody or a fragment thereof is directed to the anti-tumor antibody. The fragment of the anti-idiotypic antibody may be Fab, a Fab', a F(ab')2, a Fv, a scFv, a single domain antibody, or a diabody, or any other epitope binding fragment. An anti-idiotype antibody (also referred to herein as "anti-idiotypic antibody") in general is directed against the antigen binding site, i.e. the variable region, of a therapeutic antibody, which may be the comple-mentary determining region. The fragment of the antibody can be in the range of 0.5 kDa-50 kDa. In an embodiment, the antibody is about 15 kDa. In an embodiment, the antibody is a single domain antibody (nanobody) containing only $V_HH$. The anti-idiotypic antibody has a binding affinity for the anti-tumor antibody that may be expressed in terms of dissociation constant ($K_D$). In various embodiments, the $K_D$ of the anti-idiotypic antibody can be from 5 pM to 10 nM, 10 pM to 10 nM, 5 pM to 50 nM, 5 pM to 500 pM, 10 pM to 100 pM and so on. For example, in embodiments, the $K_D$ can be from 5 pM to 1 nM or 5 pM to 100 pM. In an embodiment, the anti-idiotypic antibody is a Camelid single domain antibody—also termed as a nanobody. These anti-bodies possess many characteristics that are ideal for the present competitive inhibition approach. Single domain anti-bodies are a small antibody format (~14 kDa), are highly stable, can be expressed in *E. coli* and can be humanized to limit immunogenicity. Additionally, camelid immunization and phage display technologies allow rapid and inexpensive development of novel inhibitors. In an embodiment, the anti-idiotypic antibody, a single domain antibody (sdAb) is an antigen blocking anti-idiotypic antibody. In an embodi-ment, the sdAb is specific for the paratope of the therapeutic antibody both to prevent antigen binding as well as limit non-specific binding to endogenous antibody. An example of an anti-diotypic antibody is 1HE, which is directed against trastuzumab. Other anti-idiotypic antibody formats may be used including VNAR idiotypes for cetuximab and mata-zumab PMID 28852148, Idiotypic peptides (commonly called mimotopes) against trastuzumab PMID: 15536075, 17513761, 17579068, cetuximab PMID: 20514015, 16288119, Panitumumab PMID: 27659529, idiotypic scFv for trastuzumab PMID 15138490, antigen epitopes (e.g. V529-P625 of HER2 PMID: 29253024). Derivatives of any of the anti-andiotypic antibodies may also be used. Such derivatives may have the following features: less than 50 kDa and preferably less than 15 kDa and monovalent.

Derivatives of anti-idiotypic antibodies may be identified from construction of phage libraries and then identification of relevant colonies by multiple rounds of panning using the relevant antigen. Affinity and identity of the clones may be carried out by screening using standard methods, such as ELISA, radioligand binding assays, surface plasmon reso-nance and the like. Sequencing of the identified colonies can be carried out and compared with the original antibody sequence to identify mutations.

In an embodiment, the anti-tumor antibody is directed to HER2 and the anti-idiotypic antibody is 1HE or derivatives thereof, wherein the derivatives bind to the HER2 antibody exhibiting a $K_D$ in the range of have 5 pM-50 nM>5 pM-500 pM. For example, the $K_D$ may be 10 pM-100 pM, or 10 pM-1 nM. The sequences of derivatives of 1HE that have been identified, and characterized, provide information on the paratopes of 1HE that are responsible for trastuzumab binding. This is described in further detail in Example 2. The center of CDR2 appears to be critical for high-affinity binding to trastuzumab, as most of the clones with faster dissociation rates have mutations at [54]NGDST[58] (SEQ ID NO:4) with the amino acid numbers 54 and 58 correspond-ing to the amino acids in SEQ ID NO:1. Therefore, 1HE mutants with faster dissociation rate constants may be rationally designed through site-directed-mutagenesis at the [54]NGDST[58] (SEQ ID NO:4) motif of CDR2.

Figure 12:
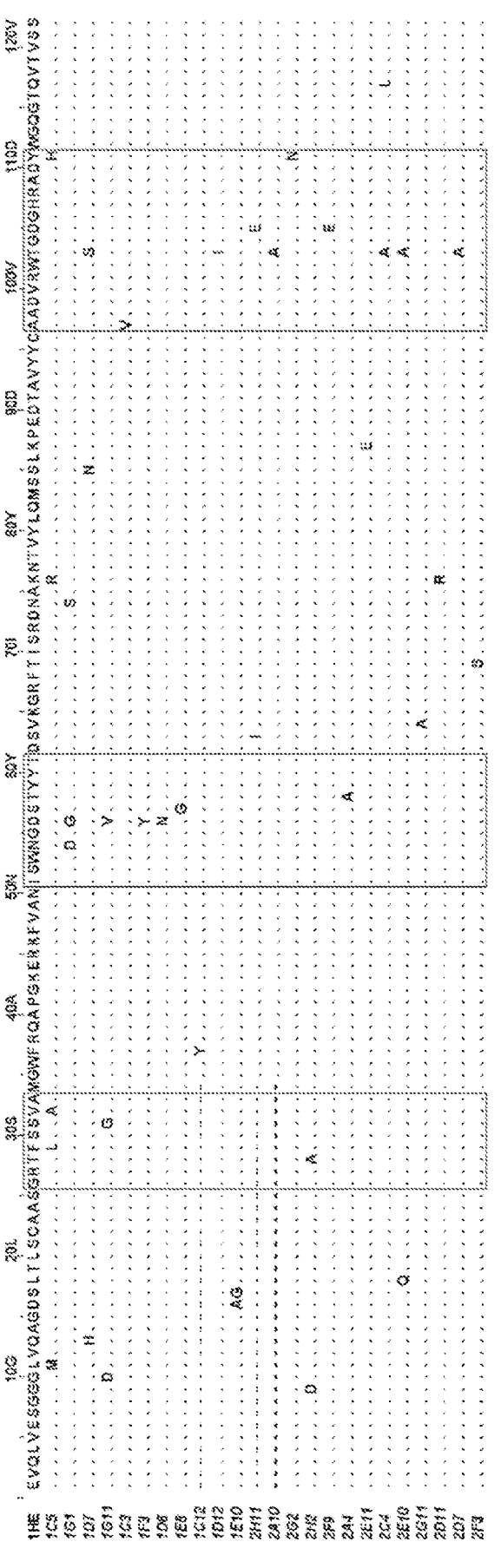
FIG. 12. Protein sequences of 1HE mutants. Protein sequences from colonies selected from the low and high-panning method are shown. Mutants from the low-affinity panning start with a 1 and mutants from the high-affinity panning start with a 2. The letter and second number correspond to the ELISA plate from FIGS. 10 and 11 for the low and high panning, respectively. The sequence of 1HE is SEQ ID NO:2. The boxed sequences in the 1HE row represent from left to right CDR1, CDR2 and CDR3 respectively. Mutations in the sequence of SEQ ID NO:2 are shown for each colony (may be referred to herein as derivative of 1HE).
Figure 13A:
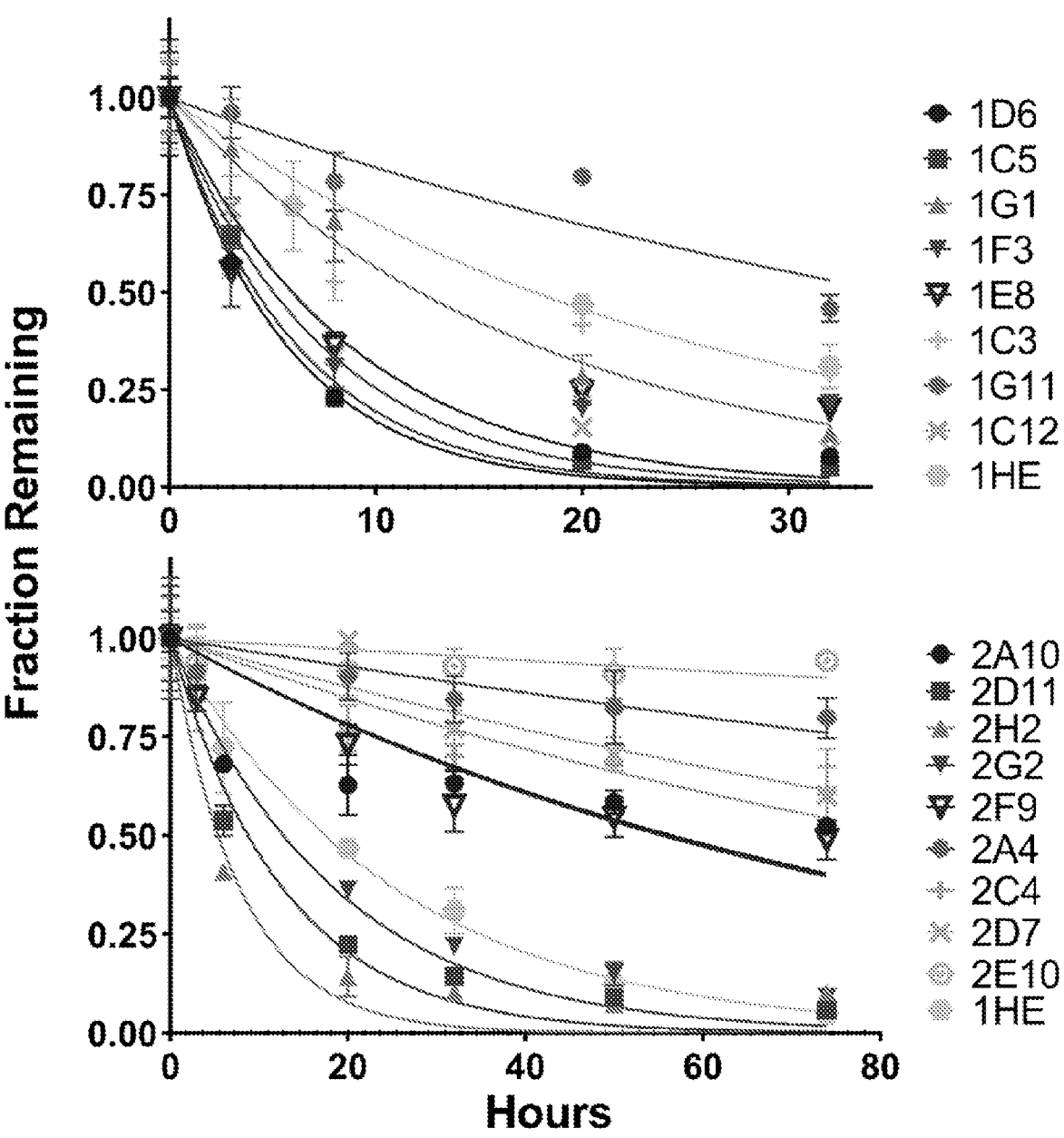
FIGS. 13A and B: Dissociation ELISA. The fractional change in absorbance is plotted over time following incubation with either 500 nM trastuzumab (top panel) or 1 μM 1HE (bottom panel) in 13A. Points represent the mean of samples in triplicate with standard deviation error bars. Lines represent the best-fit monoexponential decay for individual mutants. Half-life values are shown for the various mutants in 13B.

In some embodiments, the present disclosure provides mutants of 1HE, wherein the mutants have the sequence of SEQ ID NO:1 or the sequence of SEQ ID NO:2, wherein from 1 to 10 amino acids are substituted with another amino acid. In embodiments, 1, 2, 3, 4, 5, 6, 7, 8, 9 or 10 amino acids may be substituted. In embodiments, the derivative may have at least 50%, at least 60%, at least 70%, at least 80%, at least 90% or at least 95% homology with the sequence of SEQ ID NO:1 or the sequence of SEQ ID NO:2. In some embodiments, the present disclosure provides mutants of 1HE, wherein the mutants have the sequence of SEQ ID NO:1 or SEQ ID NO:2, except that one or more of [54]NGDST[58] (SEQ ID NO:4) are mutated in CDR2. In embodiments, only one or two amino acids from the [54]NGDST[58] (SEQ ID NO:4) motif are mutated. Examples of such mutations are shown in FIG. 12. Further, in the CDR3 sequence [103]TGDGHRADY[111] (SEQ ID NO:5), the A and D residues are considered to be critical for trastuzumab bind-ing, since none of the sequenced colonies had mutations at these residues. In embodiments, this disclosure provides 1HE mutants where one or more (e.g., up to 5) amino acids are mutated except that A and D in CDR 3 in the motif [103]TGDGHRADY[111] (SEQ ID NO:5) are not mutated. Threonine 103 was observed to be a common mutation site among the mutants with slower dissociation rate constants, relative to wild-type 1HE. Specifically, six mutants had non-conservative mutations of threonine to alanine, serine, or isoleucine. As such, if slow-dissociation rate mutants are desired (i.e., high affinity), then a mutation can be made at the T103 position. Based on the sequence of the mutants provided here and the design guidance, rational design of competitive inhibitors of desired affinity can be generated. In an embodiment, one or more of the first 33 amino acids in SEQ ID NO:1 or SEQ ID NO:2 may be deleted. In an embodiment, the first 33 amino acids are deleted. Examples of such mutants are 1C1, 2H11 and 2A10 (See FIG. 12). In embodiments, the derivatives of 1HE (SEQ ID NO:2) may comprise sequences having CDR regions that are at least 50%, at least 60%, at least 70%, at least 75%, at least 80%, at least 90%, and 95%, identical to the CDR1, CDR2, and CDR3 sequences set forth in SEQ ID NOs: 6, 7 and 8. In an embodiment, this disclosure provides 1HE mutants that have a T½ (dissociation half-life) of from 3.5 to about 500 hours. In an embodiment, this disclosure provides 1HE mutants that have a T½ (dissociation half-life) of from about 3 to about 500 hours. In an embodiment, this disclosure provides 1HE mutants that have a T½ (dissociation half-life) of from 3 to 480 hours. In some embodiments, the low affinity (fast dissociating) mutants may have a T½ of from about 4 hours to about 16 hours. In some embodiments, the high affinity (slow dissociating) mutants may have a T½ of from 17 hours to about 480 hours. In an embodiment, the low affinity mutants may have a T½ of 1 to 10 hours and the high affinity mutants may have a T½ of 11 to 100 hours. In an embodiment, the low affinity mutants may have a T½ of 1 to 10 hours and the high affinity mutants may have a T½ of 10.1 to 100 hours. In an embodiment, the low affinity mutants may have a T½ of 1 to 10 hours and the high affinity mutants may have a T½ of 11 to 480 hours. In an embodiment, the low affinity mutants may have a T½ of 1 to 10 hours and the high affinity mutants may have a T½ of 10.1 to 480 hours. In various embodiments, the derivatives of 1HE may have one or more features described above in this paragraph.

The sequences of any of the antibodies or fragments described herein may include a poly histidine tag and/or amino acids left from cloning, or the sequences may be used without the poly histidine tag (e.g., to reduce immunogenicity) and cloning related amino acids. As such any specific sequences disclosed here also include the corresponding sequences without the poly histidine tags and the cloning related amino acids.

In an aspect, this disclosure provides compositions comprising the anti-tumor antibody and anti-idiotypic antibody. These may be present in the same composition or different compositions. The antibodies may be present in a lyophilized form. When they interact, the anti-tumor antibody and the anti-idiotypic antibody exhibit reversible binding.

In an aspect, the disclosure provides pharmaceutical compositions comprising the antibodies as described herein. The formulations typically contain physiologically acceptable carriers, excipients or stabilizers and may be in the form of aqueous solutions, lyophilized or other dried or solid formulations. Examples of suitable pharmaceutical preparation components can be found in Remington: The Science and Practice of Pharmacy 20th edition (2000). Acceptable carriers, excipients, or stabilizers are nontoxic to recipients at the dosages and concentrations employed, and include buffers such as phosphate, citrate, histidine and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™, polyethylene glycol (PEG) and the like. In an embodiment, the pharmaceutical composition may comprise buffer components and stabilizers, including, but not limited to, sucrose, polysorbate 20, NaCl, KCl, sodium acetate, sodium phosphate, arginine, lysine, trehalose, glycerol, and maltose.

In an aspect, this disclosure provides methods for inhibiting or reducing the growth of tumors. The tumors may be cancerous. The method comprises administering to an individual in need of treatment: i) an anti-tumor antibody, alone or conjugated to a cytotoxic agent, and ii) an anti-idiotypic antibody, wherein the anti-idiotypic antibody is directed to the anti-tumor antibody. The anti-tumor antibody (alone or conjugated to a cytotoxic agent) and the anti-idiotypic antibody are administered such that they are present in a state of reversible binding at the tumor site and therefore provide transient competitive inhibition.

In an embodiment, the method comprises administering to an individual who is already on an anti-tumor antibody therapy for cancer a composition comprising an anti-idiotypic antibody directed to the anti-tumor antibody. For example, anti-idiotypic antibodies (e.g., 1HE or derivative thereof) may be administered to individuals are currently undergoing therapy comprising administration of anti-tumor antibodies (e.g., trastuzumab or T-DM1 or other anti-HER2 antibodies or ADCs).

Compositions comprising the anti-tumor antibody and the anti-idiotypic antibody may be administered together or independently, using any suitable route including parenteral, cutaneous (including subcutaneous), intrapulmonary, and intranasal, transmucosal and the like. Parenteral infusions include intramuscular, intravenous, intraarterial, intraperitoneal, or subcutaneous administration. Compositions may be delivered to the site of tumor directly or may be delivered intratumorally. The administration may be carried out in a continuous manner or may be intermittent. Appropriate dosage will depend upon the particular tumor being treated, the specifics and condition of the individual patient, the mode of administration etc. Determination of appropriate dosage is within the purview of one skilled in the art, such as a treating physician.

The anti-tumor antibody and the anti-idiotypic antibody may be administered as a single composition or may be administered as separate compositions. When administered as separate compositions, they may be administered sequentially or concurrently. The two compositions may be administered at the same or different times, by the same or different routes, for same or different lengths of time, on the same or different regimens so long as there is overlap of the two at the tumor site such that the two can interact and be present in a reversibly bound state. In an embodiment, irrespective of the administration regimens, the anti-tumor antibody and the anti-idiotypic antibody are present in a reversibly bound state at or near the tumor to provide transient competitive binding. As such, the routes of administrations or the frequency of administrations of the anti-tumor antibody and the anti-idiotypic antibody may be independent of each other so long as the two can reversibly bind at the tumor site. For example, in an embodiment, the anti-tumor antibody may be administered intravenously and the anti-idiotypic antibody may be administered via a cutaneous route, such as subcutaneously, intradermal, transdermal, and the like. If multiple administrations of the anti-tumor antibody or the anti-idiotypic antibody are to be carried out such multiple administrations can be done via different routes. For example, a first administration of an anti-idiotypic antibody may be done i.v., while subsequent administration may be done by another route, such as via a cutaneous route. A first administration of the anti-tumor antibody and the anti-idiotypic antibody may be done in any order if they are administered as separate compositions. For example, the anti-tumor antibody may be administered first or the anti-idiotypic antibody may be administered first, or they may be administered at the same time or their administrations may overlap.

The anti-idiotypic antibody may be selected based on the affinity to the anti-tumor antibody. For example, a fast dissociating (low affinity) antibody may be desirable if the anti-idiotypic antibody and the anti-tumor antibody are being delivered close to the tumor, such as by intraperitoneal administration or administration at or near a tumor (including intratumoral administration). As a further example, a fast dissociating derivative of 1HE may be used when the anti-tumor cytotoxin conjugate is radiolabeled, such as $^{212}$Pb-TCMC-Trastuzumab (Meredity et al., Am. J. Clin. Oncol., 2018, 41:716-721). Similarly, for other anti-tumor antibodies or conjugates delivered at or near or within the tumor, fast dissociating anti-idiotypic antibodies may be used. In contrast, if the wider application is desired, such as if the anti-tumor antibody (or conjugate) is to be delivered i.v., then a slow dissociating (high affinity) anti-idiotypic antibody may be used. In some embodiments, a combination (cocktail) of anti-idiotypic antibodies with different dissociation rates may be used. For example, 1HE derivative combination which may one or more of antibodies in FIG. 12 may be used.

In an embodiment, the amount of the combination of the anti-tumor antibody and the anti-idiotypic antibody is an amount sufficient to reduce the growth of the tumor (or prevent growth of the tumor) by at least 10% more than that expected with the anti-tumor antibody alone at the same concentration as used in the combination. In embodiments, the reduction in growth may be 20%, 30%, 40%, 50% or more.

The amount of anti-tumor antibody and the anti-idiotypic antibody (or fragments thereof) can be administered to an individual in need of treatment at a dose that is effective to treat a solid tumor. In general, suitable dosages of the antibodies or fragments thereof can range from about 0.1 mg/kg to 100 mg/kg. Examples of dosages include 0.1, 0.5, 1, 5, 10, 15, 20, 25, 30, 35, 40, 45, 50, 55, 60, 65, 70, 75, 80, 85, 90, 95 and 100 mg/kg. A variety of dosage regimens are contemplated including dosage regimens in which the antibody may be administered repeatedly, e.g., on a daily, weekly or monthly schedule, over a short period or an extended period of time, e.g., months to years (e.g., maintenance therapy). The range for administration of the anti-idiotypic antibody may be from 0.01-100 mg/kg. A suitable ratio of the anti-idiotypic antibody and the anti-tumor antigen antibody may be determined by one skilled in the art. In an embodiment, the optimal ratio can be from 1:1 to 10:1 for anti-idiotypic sdAb:anti-tumor Ab. For example, the ratio may be 10:1, 7:1, 5:1, 3:1, 2:1, 1:1, 1:2, 1:3, 1:5, 1:7, 1:10, and all ratios therebetween for anti-idiotypic antibody:anti-tumor antibody.

The present compositions and methods also include half-life extension strategies to increase plasma half-life of the anti-idiotypic inhibitors including fusion of moieties to the anti-idiotypic sdAb that bind blood components such as albumin, red blood cells or endogenous IgG as well as PASylation and PEGylation. Thus, in embodiments, the anti-idiotypic antibody may by fused to albumin, red blood cells or endogenous IgG, or fragments thereof, or may be PASylated and/or PEGylated. In an embodiment, the antibodies or fragments do not contain a polyhistidine tag.

The present composition/compositions may be administered alone or in combination with other types of treatments (e.g., surgical resection, radiation therapy, chemotherapy, hormonal therapy, immunotherapy or other anti-tumor agents).

The present compositions may be used for any type of cancer, including carcinoma, lymphoma, sarcoma, melanoma and leukemia. Non-limiting examples include any type of tumor including squamous cell cancer, small-cell lung cancer, non-small cell lung cancer, adenocarcinoma of the lung, squamous carcinoma of the lung, cancer of the peritoneum, myeloma (including multiple myeloma), hepatocellular cancer, gastrointestinal cancer, pancreatic cancer, glioblastoma/glioma (e.g., anaplastic astrocytoma, glioblastoma multiforme, anaplastic oligodendroglioma, anaplastic oligodendroastrocytoma), cervical cancer, ovarian cancer, liver cancer, bladder cancer, hepatoma, breast cancer, brain cancer, colon cancer, colorectal cancer, endometrial or uterine carcinoma, salivary gland carcinoma, kidney cancer, liver cancer, prostate cancer, vulval cancer, thyroid cancer, hepatic carcinoma, ovarian cancer, prostate cancer, cervical cancer, and various types of head and neck cancer.

In an aspect, the present disclosure provides kits for treatment of cancers. The kits comprise in separate sterile containers anti-tumor antibody and anti-idiotypic antibody (or another inhibitor of the binding of the anti-tumor antibody with its antigen), and optionally buffers or pharmaceutical carriers for dilution or preparing solutions, and optionally, instructions for use. The antibodies may be present in a lyophilized form and separate containers may be provided for reconstituting the antibodies prior to use. The reconstitution media may be buffer or saline or water etc. In an embodiment, the kit comprises in separate containers, anti-HER2 antibody, and an anti-idiotypic antibody. For example, the kit may comprise trastuzumab or T-DM1, and 1HE or a mutant (derivative) thereof. In an embodiment, the kit may comprise the anti-tumor antibody and the anti-idiotypic antibody in the same container in a lyophilized form, and reconstitution medium for reconstituting the antibody composition prior to use, and optionally instructions for preparation of the composition and use of the compositions.

Some embodiments of the present disclosure are provided in the examples below.

Example 1. A composition comprising i) an anti-tumor antibody or an antigen binding fragment thereof, alone or conjugated to a cytotoxic agent, and ii) an anti-idiotypic antibody or a fragment thereof, wherein the anti-idiotypic antibody or a fragment thereof is directed to the anti-tumor antibody or its antigen binding fragment.

Example 2. The composition of example 1, wherein the anti-idiotypic antibody has a molecular weight of about 15 kDa.

Example 3. The composition of example 1, wherein the anti-idiotypic antibody is a single domain antibody.

Example 4. The composition of example 1, wherein the anti-tumor antibody is a monoclonal antibody.

Example 5. The composition of example 4, wherein the monoclonal antibody is conjugated to a cytotoxic agent.

Example 6. The composition of example 1, wherein the antibody is an antibody drug conjugate.

Example 7. The composition of example 1, comprising a pharmaceutical carrier.

Example 8. The composition of example 1, wherein i) is trastuzumab or T-DM1, and ii) is 1H.

Example 9. A method for reducing or preventing the growth of a tumor comprising administering to an individual in need of treatment: i) an anti-tumor antibody or an antigen binding fragment thereof, alone or conjugated to a cytotoxic agent, and ii) an anti-idiotypic antibody or a fragment thereof, wherein the anti-idiotypic antibody or a fragment thereof is directed to the anti-tumor antibody or its antigen binding fragment.

Example 10. The method of example 9, wherein i) and ii) are administered as separate compositions.

Example 11. The method of example 9, wherein i) and ii) are administered in the same composition.

Example 12. The method of example 9, wherein i) is trastuzumab or T-DM1, and ii) is 1HE.

The invention is further demonstrated by way of the figures and data presented herein.

Example 1

Materials and Methods

Expression and Purification of 1HE

The amino acid sequence for 1HE was obtained from the original publication by Alvarez-Reuda and colleagues (Alvarez-Rueda et al., Vaccine, 2009. 27(35): p. 4826-4833) (Sequence provided as SEQ ID NO:2). A codon optimized DNA sequence for *E. coli* expression was synthesized by GeneArt (ThermoFisher, Rockford, IL), (SEQ ID NO:3) ligated into the plasmid pET22b(+) (Millipore-Sigma, 69744) at the XhoI and NdeI restriction enzyme sites and transformed into the *E. coli* strain BL21(DE3). To express 1HE, cells containing the DNA construct are struck onto an LB agar plate containing 100 µg/ml of ampicillin and incubated at 37° C. for 18 hours. Using a sterile pipet tip, a single colony is lifted and transferred into a 10 ml starter culture of LB media. The starter culture is transferred to a shaker incubator at 37° C. overnight. The starter culture is then transferred into a 1 L seeder culture of terrific broth and grown to an optical density of 0.6-0.8. Once the proper cell density is reached the culture is induced with 1 mM IPTG and incubated (20° C., 21 hours, 180 RPM). After 18 hours the cells are centrifuged at 15,000×g for 10 minutes, excess media is decanted, and the pelleted cells are lysed using BugBuster (Millipore-Sigma, 70584) and centrifuged at 10,000×g for 20 minutes. The insoluble pellet, containing 1HE inclusion bodies, is then solubilized in a 8 M urea buffer pH 10 containing 50 mM Tris-HCl and 500 mM NaCl. Purification is completed using a HisPur™ Ni-NTA Spin Column (Thermo Scientific, 88226) with on-column refolding using a stepwise urea gradient (8 M, 6 M, 4 M, 2 M, 0 M). After elution 1HE is dialyzed in PBS to remove excess imidazole.

The following protocol was also alternatively used. Briefly, a glycerol stock of SHuffle cells (New England Biolabs, Ipswich, MA, C3029J) transformed with 1HE ligated in the Pet22b(+) plasmid (Millipore-Sigma, Burlington, MA, 69744) was removed from storage at −80° C. and a small volume spread over a lysogeny broth (LB) agar plate with 100 µg/ml ampicillin. The next day a single colony was selected and inoculated into an LB medium starter culture with 100 ug/ml ampicillin and grown in a shaker incubator at 30° C. for 18 hours. The starter culture was diluted 1 to 100 into LB medium with 100 µg/ml ampicillin and cells grown to a density of 0.6-0.8 and expression induced with 1 mm isopropyl β-d-1-thiogalactopyranoside (IPTG) for 18 hours at 16° C. Cells were pelleted, lysed, and purified with a 3 mL HisPur™ Ni-NTA spin column (Thermo Fisher Scientific, Waltham, MA, 88226). Eluted protein was dialyzed into a 5 mM disodium phosphate buffer pH 6.8 overnight and the dialyzed product run over a ceramic hydroxyapatite (CHT) column with a 0-100% 500 mM disodium phosphate elution gradient over 100 minutes. Collected fractions were analyzed with sodium dodecyl sulfate-polyacrylamide gel electrophoresis (SDS-PAGE) and fractions containing 1HE combined and dialyzed into phosphate buffered saline pH 7.4 (PBS) overnight.

Amino Acid Sequence for 1HE is provided below (SEQ ID NO:1), wherein bolded amino acids represent the amino acids contributed for XhoI restriction site and the hexahistidine tag that is encoded as part of the Pet22b plasmid used for purification.
EVQLVESGGGLVQAGDSLTLSCAASGRTFSS-
VAMGWFRQAPGKERKFVANISWNGDS
TYYTDSVKGRFTISRDNAKNTVYLQMSSLKPED-
TAVYYCAADVRWTGDGHRADYW
GQGTQVTVSSLEHHHHHH (SEQ ID NO:1). The sequence of 1HE without the restriction site amino acids and hexahistidine tag is provided below as SEQ ID NO:2
EVQLVESGGGLVQAGDSLTLSCAASGRTFSS-
VAMGWFRQAPGKERKFVANISWNGDS
TYYTDSVKGRFTISRDNAKNTVYLQMSSLKPED-
TAVYYCAADVRWTGDGHRADYW GQGTQVTVSS
(SEQ ID NO:2). This is also shown in FIG. 12. In this sequence, CDR1 is GRTFSSVA (SEQ ID NO:6), CDR2 is ISWNGDSTYYT (SEQ ID NO:7), and CDR3 is AAD-VRWTGDGHRADY (SEQ ID NO:8). These are shown as boxed sequences in FIG. 12.

The genetic Sequence of 1HE is shown below, wherein restriction enzyme sites are bolded (SEQ ID NO:3).

```
                                       (SEQ ID NO: 3)
CATATGGAAGTTCAGCTGGTTGAAAGCGGTGGTGGTCTGGTTCAGGCAGG

CGATAGTCTGACCCTGAGCTGTGCAGCAAGCGGTCGTACCTTTAGCAGCG

TTGCAATGGGTTGGTTTCGTCAGGCACCGGGTAAAGAACGTAAATTTGTT

GCAAATATTAGCTGGAATGGCGACAGCACCTATTATACCGATAGCGTTAA

AGGTCGTTTTACCATTAGCCGTGATAATGCCAAAAATACCGTTTACCTGC

AGATGAGCAGCCTGAAACCGGAAGATACCGCAGTGTATTATTGTGCAGCA

GATGTTCGTTGGACCGGTGATGGTCATCGTGCAGATTATTGGGGTCAGGG

CACCCAGGTTACCGTTAGCAGCCTCGAG
```

Surface Plasmon Resonance

An SR7500DC SPR (Reichert, Depew, N.Y.) was utilized for kinetic binding assessment of 1HE:trastuzumab binding kinetics. Trastuzumab was immobilized on a CMS chip (Reichert, Depew, NY, Part #: 13206066) through amine coupling. A mobile phase of 0.05% Tween-20 PBS pH 7.4 was used at a flow rate of 25 µL/minute. Evaluation of 1HE-trastuzumab binding was completed with a 10-hour dissociation time with 1HE injections at concentrations of 10, 20, and 35 nM. Association and dissociation rate constants were determined using a 1:1 Langmuir binding model in the biosensor data analysis software Scrubber (BioLogic Software, Canberra, Australia).

Radiolabeling of Trastuzumab and 1HE

Trastuzumab and 1HE were radiolabeled with $^{125}$I through a modified chloramine-T method described previously (Garg et al., J Pharmacokinet Pharmacodyn, 2007. 34(5): p. 687-709). Briefly, 40 µL of protein (1-2 mg/mL in pH 7.4 PBS) was combined with 10 µL of Na$^{125}$I (100 mCi/mL) (PerkinElmer, Waltham, MA), and subsequently reacted with 20 µL of chloramine-T (1 mg/mL in pH 7.4 PBS). After 90 seconds, the reaction was terminated by addition of 40 µL of 10 mg/mL potassium iodide. Immediately following the reaction, gel filtration (Sephadex G-25 column, GE Healthcare Bio-Sciences, Pittsburgh, PA) was performed to separate $^{125}$I labeled intact antibody from the mixture. Activity of the $^{125}$I-protein fraction was determined through gamma counting (LKB Wallac 1272, Wallac, Turku, Finland) with purity assessed through thin layer chromatography (PE SiL-G, Whatman Ltd, Kent, England).

Assessment of 1HE Inhibition on [125]I-Trastuzumab-HER2 Binding

SKOV3 cells (ATCC, HTB-77) were grown in complete McCoys 5a media to confluency in a T75 flask and dissociated using 50 µM EDTA. Cells were pelleted (200 xg, 5 minutes) and resuspended in a 1% bovine serum albumin PBS solution and pipetted into microcentrifuge tubes (1 million cells/mL). $^{125}$I-trastuzumab was added to each tube, at a concentration of 200 pM, with increasing concentrations of 1HE. Cells were incubated at 4° C. for 90 minutes to reach binding equilibrium followed by 4 washes with 1 mL of 1% BSA PBS buffer to remove non-specific radioactivity. Cell-associated radioactivity was assessed through gamma counting. Cell-associated radioactivity normalized to a $^{125}$I-trastuzumab control (B/Bo) was fit to a 3-parameter logistic function in Graphpad Prism 7 (GraphPad, San Diego, CA).

Plasma Pharmacokinetics of Trastuzumab

Plasma pharmacokinetics of trastuzumab with and without co-administration of 1HE were assessed in male Swiss-Webster mice 4-6 weeks of age (Envigo, Indianapolis, IN). Trastuzumab was given through penile vein injection at a dose of 0.1, 1 and 10 mg/kg (n=5/group) with and without 1HE in a 1:2 molar ratio (Trastuzumab:1HE) with a tracer dose of [125]I-Trastuzumab (400 µCi/kg). Blood samples were collected through retro-orbital sampling using microcapillary tubes coated with EDTA. Plasma samples were collected following centrifugation (200xg, 5 minutes), and TCA precipitated. Plasma associated radioactivity was determined through gamma-counting with observed counts corrected for background radiation and radioactive decay. Noncompartmental analysis (WinNonlin 7, Phoenix, Pharsight Corporation, Palo Alto, CA) was used for calculation of $AUC_{(0-10\ days)}$ and clearance. Students t-test was used for statistical comparisons to determine if 1HE significantly impacted plasma pharmacokinetics within dose groups with statistical significance set at p<0.05.

Quantification of 1HE in Mouse Plasma

A indirect ELISA was developed for quantification of 1HE in mouse plasma.

Standards were prepared through dilution of a stock 1HE solution into mouse plasma, subsequently, samples were diluted 100x in PBS to create working standards over a range of 0.5-15 ng/ml. The precision and accuracy of the ELISA was determined through recovery of 1HE quality control samples prepared identically to the standards at 1, 8, and 13 ng/ml. Standards and quality control samples were prepared and run for an individual plate for each assay. The ELISA plate was prepared by binding 250 µL of trastuzumab at 4 µg/mL in a 20 mM $Na_2HPO_4$ buffer (no pH adjustment) onto a 96-well NUNC Maxisorb plate (Thermo Scientific, 439454) overnight at 4° C. The following day unreacted sites were blocked for 2 hours using a 1% BSA solution at room temperature. Plates were washed 3x with PB-Tween 0.5% pH 7.2 and 2x with dH2O. Next, unknown plasma samples were added in triplicate along with standards and quality control samples (250 uL/well) and incubated for 2 hours at room temperature. Following incubation, the wells were washed as described above and a anti-HIS secondary antibody (Abcam, ab49746) diluted 1:10,000 in 1% BSA-PBS was added to each well (250 µL/well) for 1 hour at room temperature. The plate was washed and 4 mg/ml para-nitrophenyl phosphate in 10 mM diethanolamine pH 9.8 added to each well (250 µL/well). Change in absorbance at 405 nm was assessed for 10 minutes with a SpectraMax 340PC plate reader (Molecular Devices, San Jose, CA). Standard curves were obtained through fitting of the dA/dt to a 4-parameter logistic function in GraphPad Prism 7.

1HE Pharmacokinetics

1HE pharmacokinetics were assessed following a 0.1, 1 and 10 mg/kg dose in male Swiss-Webster mice 4-6 weeks of age (Envigo, Indianapolis, IN). Blood samples were collected through retro-orbital or submandibular sampling and plasma samples collected following centrifugation (200xg, 5 minutes). 1HE concentration in plasma was assessed using the indirect ELISA described above. To determine the pharmacokinetics of 1HE when administered with trastuzumab, 1HE was administered with a tracer dose of [125]I-1HE with 1 mg/kg trastuzumab in 3 separate dose ratios of 1:0.2, 1:2, 1:20 (Trastuzumab:1HE). Blood samples were collected through retro-orbital sampling using microcapillary tubes coated with EDTA. Plasma samples were collected following centrifugation (200xg, 5 minutes), and TCA precipitated. Following TCA-precipitation plasma associated radioactivity was determined through gamma-counting with observed counts corrected for background radiation and radioactive decay.

Immunofluorescence Histology

Male NOD-SCID mice (Charles-River, Wilmington, MA) were subcutaneously injected with 2 million SKOV3 (ATCC, HTB-77) cells in DPBS in the right flank. Once tumors reached an average size of 200 mm³ mice were intravenously injected with 2 mg/kg trastuzumab alone or with 1HE in a 1:2 molar ratio (Trastuzumab:1HE). Mice were sacrificed 24 hours post-dosing, tumors excised, covered in OCT-TEK media (VWR, 25608-930) and frozen in liquid nitrogen cooled isopentane. Tumors were sectioned at 10 µM, fixed in −20° C. acetone and air-dried for 10 minutes. Sections were outlined with a PAP pen and rehydrated in PBS for 5 mins followed by primary antibody staining with rat anti-mouse CD31 (390, Invitrogen, Carlsbad, CA) and rabbit anti-human (SA5-10223, Invitrogen, Carlsbad, CA) at 1:50 and 1:500 dilutions respectively in 5% goat plasma for 2 hours at room temperature. Tumor sections were washed 3x in 0.05 Tween-PBS and incubated with secondary fluorescent antibodies, goat anti-rat Dylight 550 (SA5-10019, Invitrogen, Carlsbad, CA) and goat anti-human Alexa-Fluor 647 (A-21074, Invitrogen, Carlsbad, CA) at 1:250 and 1:500 dilutions respectively in 5% goat plasma PBS for 1 hour followed by a second round of washing. Slides were mounted in FluorSave (Millipore-Sigma, 345789) and stored at 4° C. until imaging. Tumor sections were imaged identically using an EVOS Fl autofluorescent microscope (ThermoFisher, Carlsbad, CA) with RFP and CY5 excitation cubes. Control tumor sections were treated identically, with the omission of the primary antibody incubation.

T-DM1 Efficacy

Figure 2:
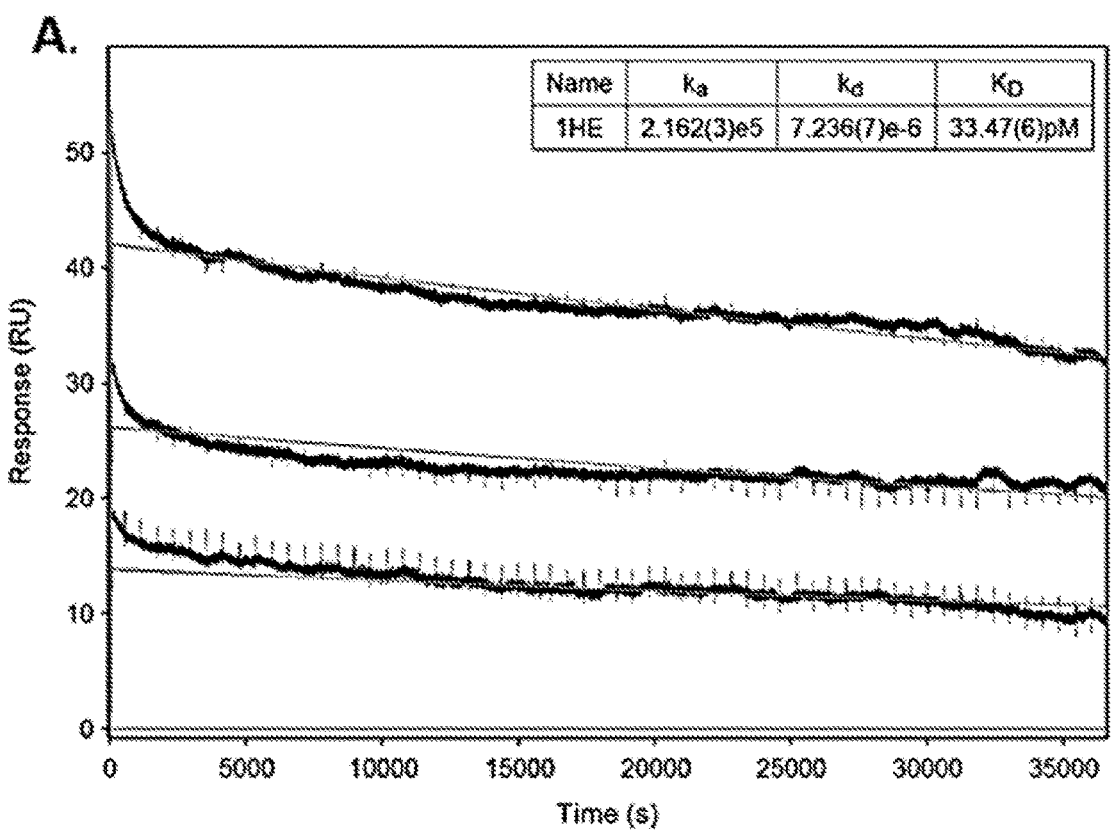
FIG. 2: 1HE binds with high affinity to trastuzumab and inhibits HER2 binding: (A) SPR sensorgram of 1HE binding to trastuzumab following an 10-hour dissociation with kinetic model fitting results in the appended table. (B) Competitive cell inhibition assay to assess the impact of 1HE on trastuzumab-HER2 binding, shown is the ratio of trastuzumab bound to SKOV3 cells (as measured by cell-associated radioactivity) when incubated with 1HE in comparison to a $^{125}$I-trastuzumab only control. Results indicate 1HE is a potent inhibitor of trastuzumab-HER2 binding with a IC50 of 129 pM. Points represent the mean of triplicate samples with standard deviation error bars.
Figure 2:
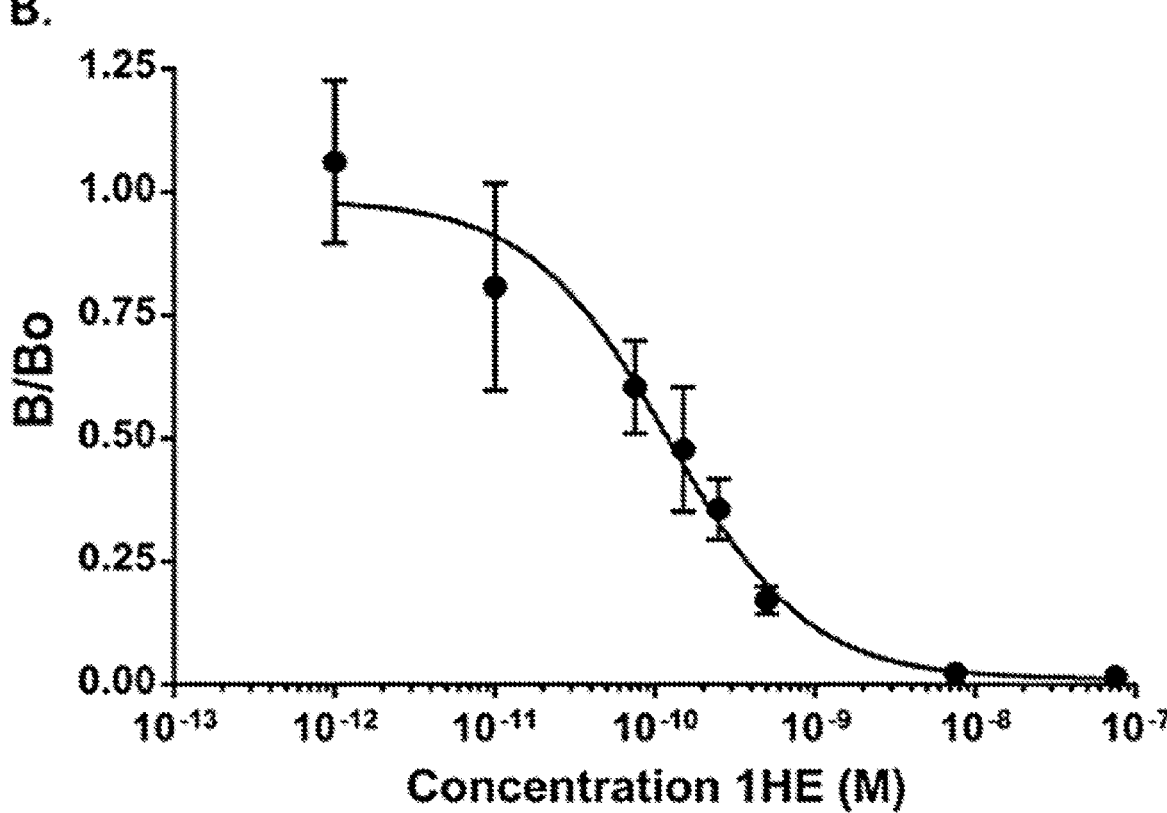
Figure 3:
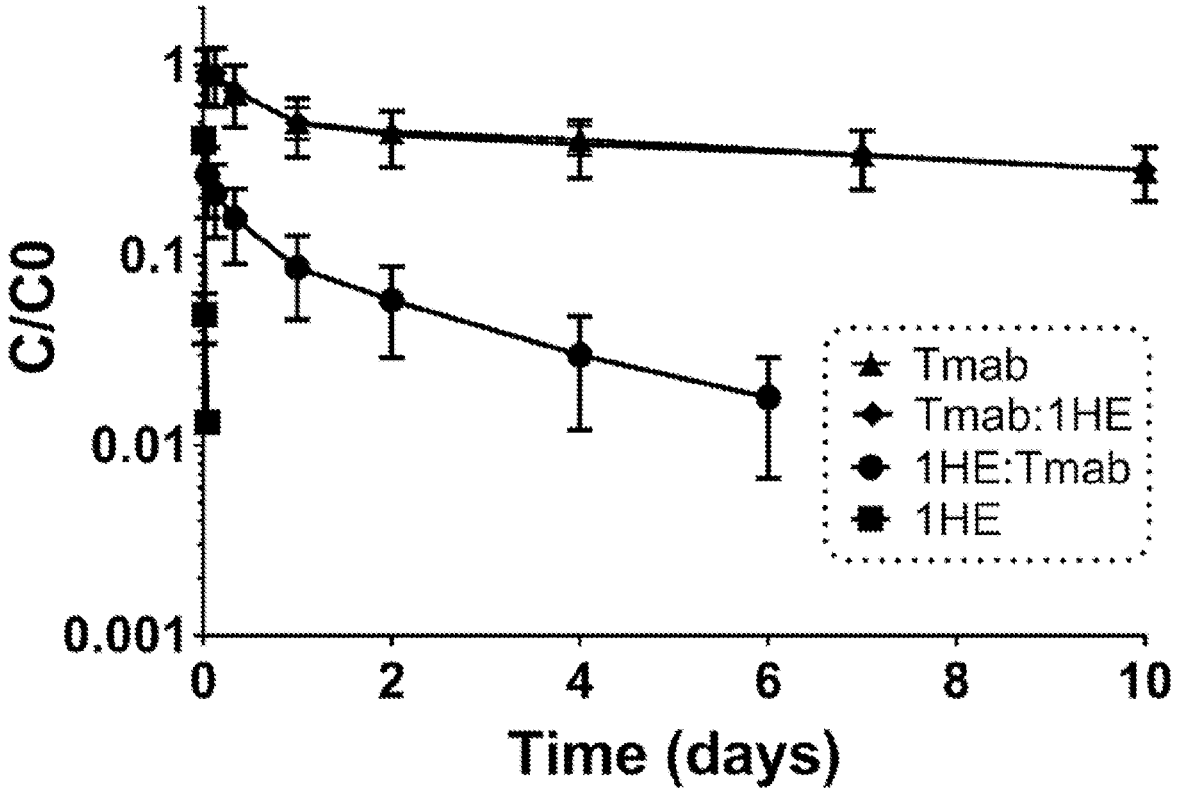
FIG. 3: Trastuzumab: 1HE pharmacokinetics with and without co-administration: For facile comparison of the impact of co-administration of 1HE with trastuzumab, a single dose group was taken from each plasma pharmacokinetic investigation and is shown plotted as the fraction of the initial concentration remaining. Trastuzumab plasma pharmacokinetics was not significantly altered when administered with 1HE. 1HE when administered alone was rapidly eliminated from plasma, consistent with expectations for a 15 kDa protein. Co-administration of 1HE with trastuzumab led to a significant extension in the half-life of 1HE with an observed terminal elimination half-life of 56 hours. Points represent the mean of 5 mice/group with standard deviation error bars. Tmab stands for trastuzumab. The Tmab:1HE profile follows trastuzumab specific pharmacokinetics when administered with 1HE whereas the 1HE:Tmab profile shows 1HE specific kinetics when administered with trastuzumab. Specifically, this means that radiolabel $^{125}$I is conjugated to either Tmab (Tmab:1HE profile) or 1HE (1HE:Tmab profile).
Figure 6:
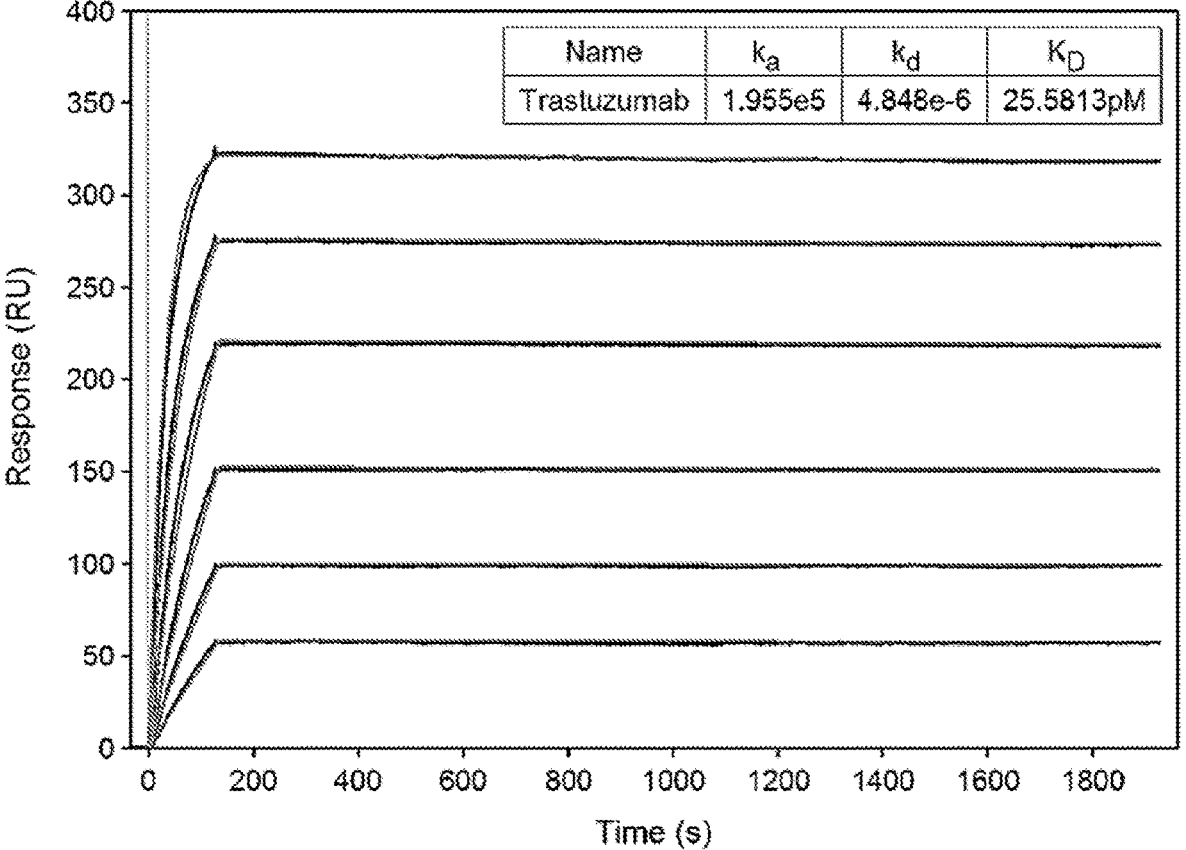
FIG. 6: An SR7500DC SPR (Reichert, Depew, N.Y.) was utilized for kinetic analysis of trastuzumab binding to HER2. HER2-Fc was immobilized on a CMS chip through amine coupling at 850 μRIU. Binding kinetics was assessed by injection of trastuzumab over the flow-cell at 5, 10, 20, 40, 80, 160 nM for 2 minutes (25 ul/min), with a 30-minute dissociation and chip regeneration between injections using a 10 mM Glycine pH 1.5 wash. Observed sensorgrams were fit to a 1:1 binding model in Scrubber to obtain association and dissociation rate constants. Due to the relatively high immobilization of HER2 the observed kinetics represent trastuzumab avidity, where both arms of trastuzumab are bound to HER2. As the rate constants observed were used for trastuzumab binding in the simulations with a 1:1 HER2:trastuzumab, it is important to have these rate constants be representative of avidity, to accurately capture the impact of the binding site barrier on trastuzumab distribution.
Figure 7:
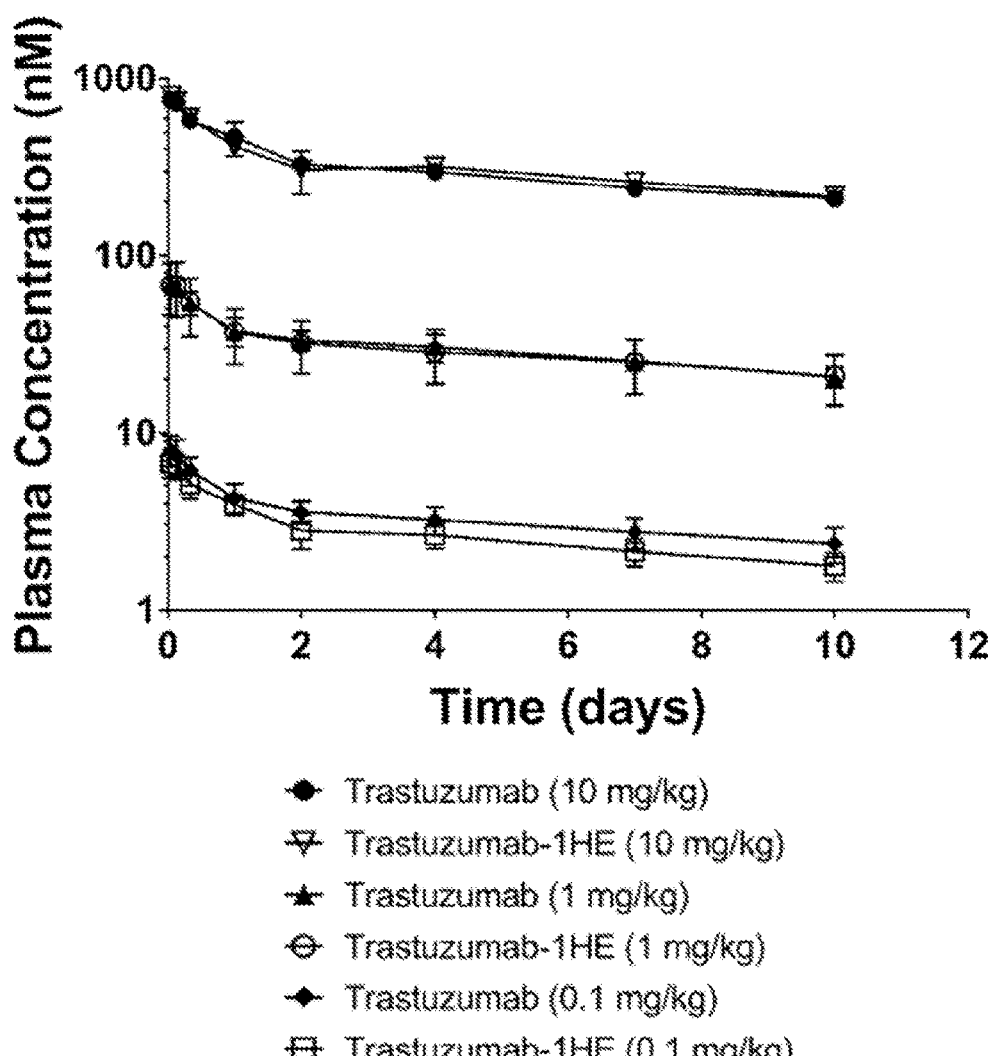
FIG. 7: Trastuzumab Pharmacokinetics with and without co-administration of 1HE. Shown in the top plot is the observed plasma pharmacokinetics of trastuzumab administered with and without 1HE (1:2 molar ratio trastuzumab to 1HE) at doses of 0.1, 1 and 10 mg/kg to Swiss-Webster mice. Shown below is the area under the plasma time profile from 1 hour to 10 days post-injection and the observed clearance for each group. Co-administration of 1HE with trastuzumab does not significantly alter trastuzumab plasma pharmacokinetics in Swiss-Webster mice.

Male NU/J mice, 4-6 weeks (The Jackson Laboratory, Bar Harbor, ME), were injected subcutaneously in the right flank with 5 million NCI-N87 cells (ATCC, CRL-5822) in 200 µl of a 1:1 matrigel (Fisher Scientific, CB-40234): RPMI 1640 solution. Tumor size was measured using digital calipers with tumor volume calculated using the formula: tumor volume=0.5*a²*b, where a is tumor width and b tumor length. Once tumor volumes reached an average of ~250 mm³ mice were split into 4 groups: saline vehicle (n=7), trastuzumab 10 mg/kg (n=7), T-DM1 1.8 mg/kg (n=9) and T-DM1:1HE 1.8 mg/kg (n=9). Mice were injected through retro-orbital injection with either 1HE (10-fold molar excess) or saline administered 30 minutes following T-DM1 injection. Tumor volumes were monitored every 2-days with mice sacrificed once tumors reached a terminal volume of 1200 mm³. Kaplan-Meier survival curves were generated in GraphPad Prism 7 and compared using the log-rank test at a significance level of P≤0.05.
Results
1HE Shows Model Inhibitor Characteristics In-Vitro
To characterize the binding kinetics of 1HE to trastuzumab an 10-hour dissociation of 1HE from trastuzumab was run using surface plasmon resonance and the observed sensorgrams fit to a 1:1 Langmuir binding model in Scrubber (FIG. 2A). The high-affinity interaction, representing the apparent binding kinetics of 1HE to trastuzumab, was fit with an equilibrium dissociation constant of 33.47 pM and a half-life of dissociation of 26.65 hours. To confirm 1HE binding to trastuzumab inhibited HER2 binding a competitive cell-based assay with $^{125}$I-trastuzumab and increasing concentrations of 1HE were completed (FIG. 2B). 1HE addition led to a reduction in trastuzumab bound to cellular HER2+, indicating 1HE is a competitive inhibitor of trastuzumab-HER2 binding. The observed IC50 (122 pM) of 1HE was approximately equal to ~50% of the concentration of trastuzumab added (200 pM), indicating the KD of 1HE to trastuzumab was ≤122 pM. The observed affinity for 1HE indicated 1HE was a suitable competitive inhibitor for in-vivo investigations. An optimal range was 10 pM to 10 nM.
Plasma Pharmacokinetics of Trastuzumab and 1HE
To determine if trastuzumab plasma pharmacokinetics would be altered with 1HE binding, trastuzumab was administered to non-tumor bearing mice, with and without 1HE, and plasma pharmacokinetics assessed. Non-compartmental analysis of the plasma pharmacokinetic time profiles indicated there was no significant difference in the $AUC_{(0-10\ days)}$ or clearance for trastuzumab administered alone or with 1HE (FIG. 7). 1HE administered alone was rapidly eliminated with less than 5% of the initial dose remaining after 20 minutes and a terminal elimination half-life of 1.16 hours. Co-administration of 1HE with trastuzumab led to a significant decrease in the elimination of 1HE, with a terminal elimination half-life of 56 hours. To compare the impact of co-administration on trastuzumab and 1HE pharmacokinetics, a plasma time profile from a single dose group from each pharmacokinetic study is shown in FIG. 3.
1HE Increases Trastuzumab Tumor Penetration
Xenograft tumors taken from mice administered 2 mg/kg trastuzumab with and without 1HE (1:2 Trastuzumab:1HE molar ratio) were stained ex-vivo for detection of trastuzumab and tumor vasculature and imaged under identical intensities. Trastuzumab (green) was restricted around vasculature (red) with only a fraction of the total tumor area staining positive for trastuzumab (FIG. 4A). Tumor sections obtained from mice administered trastuzumab and 1HE demonstrated a more homogeneous staining pattern, with a greater percentage of the tumor area staining positive for trastuzumab (FIG. 4B). Consistent with expectations, the increase in distribution of trastuzumab with 1HE led to a decrease in the fluorescence intensity of trastuzumab, as a equivalent mass of antibody was spread over a greater area. To demonstrate a whole tumor distribution pattern that was easily visualized, a tumor section taken from a mouse administered trastuzumab and trastuzumab:1HE was converted to a black and white image (FIGS. 4C and D respectively). Tumor regions in which trastuzumab fluorescence was greater than 2× the mean background of a control tumor section appears in black, with areas negative for trastuzumab staining appearing in white. Tumor sections taken from trastuzumab administered mice had positive staining that was restricted to the outer tumor rim and well-vascularized regions within the tumor (FIG. 4C). In contrast, a majority of the tumor section taken from mice administered trastuzumab with 1HE stained positive for trastuzumab (FIG. 4D).
1HE Co-Administration Improves T-DM1 Efficacy in a NCI-N87 Xenograft
The antibody-drug conjugate T-DM1 has been previously shown to be effective when occupying only a fraction of available binding sites on the gastric carcinoma cell line NCI-N87 (Cilliers et al., Cancer Res, 2018. 78(3): p. 758-768). To assess the impact of 1HE on T-DM1 efficacy xenograft-bearing mice were administered T-DM1 at a dose of 1.8 mg/kg with and without 1HE. NCI-N87 has been reported to be resistant to trastuzumab monotherapy (Cilliers et al., Cancer Res, 2018. 78(3): p. 758-768), therefore, trastuzumab was included as a additional control group for model validation. Resulting tumor growth and survival curves are shown in FIGS. 6A and B respectively. Trastuzumab did not significantly extend life-span in comparison to the control group (p=0.68). T-DM1 alone significantly improved survival from the saline group (p=0.033) but not the trastuzumab group (p=0.27). T-DM1 co-administered with 1HE had a significant increase in survival from T-DM1 alone (p=0.0054) and both the trastuzumab (p=0.004) and saline groups (p<0.0001).
Discussion
Here we describe a new strategy to overcome the binding site barrier (BSB) for trastuzumab through use of a competitive inhibitor of HER2 binding. The BSB has been implicated as a primary obstacle to therapeutic antibody distribution within solid tumors and despite having been well described for over 25 years, no clinically useful approach to overcome the BSB exists. We used trastuzumab as a model antibody for experimental validation of the competitive inhibition strategy due to its clinical relevance as both a monoclonal antibody and antibody-drug conjugate (T-DM1). For the anti-idiotypic antibody, we used a camelid single domain antibody 1H.
Fluorescence histology of xenograft tumor sections showed trastuzumab administered with 1HE was evenly distributed, with only a fraction of the total tumor area staining negative for trastuzumab. In comparison mice administered trastuzumab alone had limited tumor penetration, with positive staining for trastuzumab observed at the tumor rim and peri-vascular regions.
The present methods are applicable for anti-tumor antibodies as well as antibody-drug conjugates. We observed that 1HE significantly improved trastuzumab distribution. We also observed that co-administration of 1HE with T-DM1 significantly increased the survival of NCI-N87 tumor-bearing mice in comparison to T-DM1 alone.

Example 2

Figure 8:
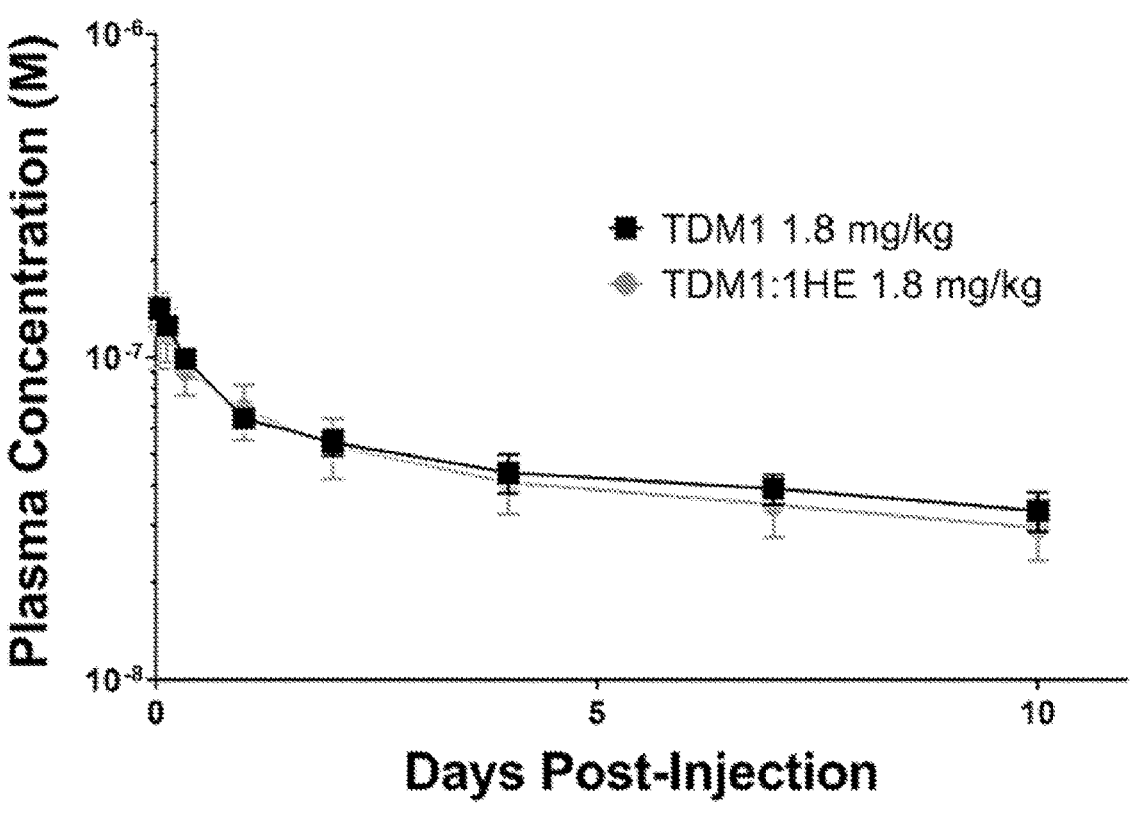
FIG. 8: T-DM1 plasma pharmacokinetics with and without 1HE co-administration. Shown the observed plasma pharmacokinetics of TDM1 administered with and without 1HE (1HE administered at a 10-fold molar excess to T-DM1 15-minutes after T-DM1 injection) at a dose of 1.8 mg/kg to Swiss-Webster mice. 1HE co-administration did not significantly alter T-DM1 plasma pharmacokinetics in Swiss-Webster mice.

This example describes the effects of 1HE on plasma pharmacokinetics on TDM1 and also shows the timecourse of 1HE dissociation from trastuzumab (through use of radiolabeled 1HE).
Swiss-Webster mice (n=5/group) were injected with T-DM1 with a 400 uCi/kg tracer dose of $^{125}$I-TDM1. 15 minutes after TDM1 injection, 1HE was administered intravenously in a 10:1 molar ratio, consistent with the dose used for the NCI-N87 efficacy study. The T-DM1 control was administered a saline vehicle of equivalent volume 15 minutes after T-DM1 injection. As shown in FIG. 8, co-administration of 1HE did not significantly alter the plasma pharmacokinetics of T-DM1.

Figure 9:
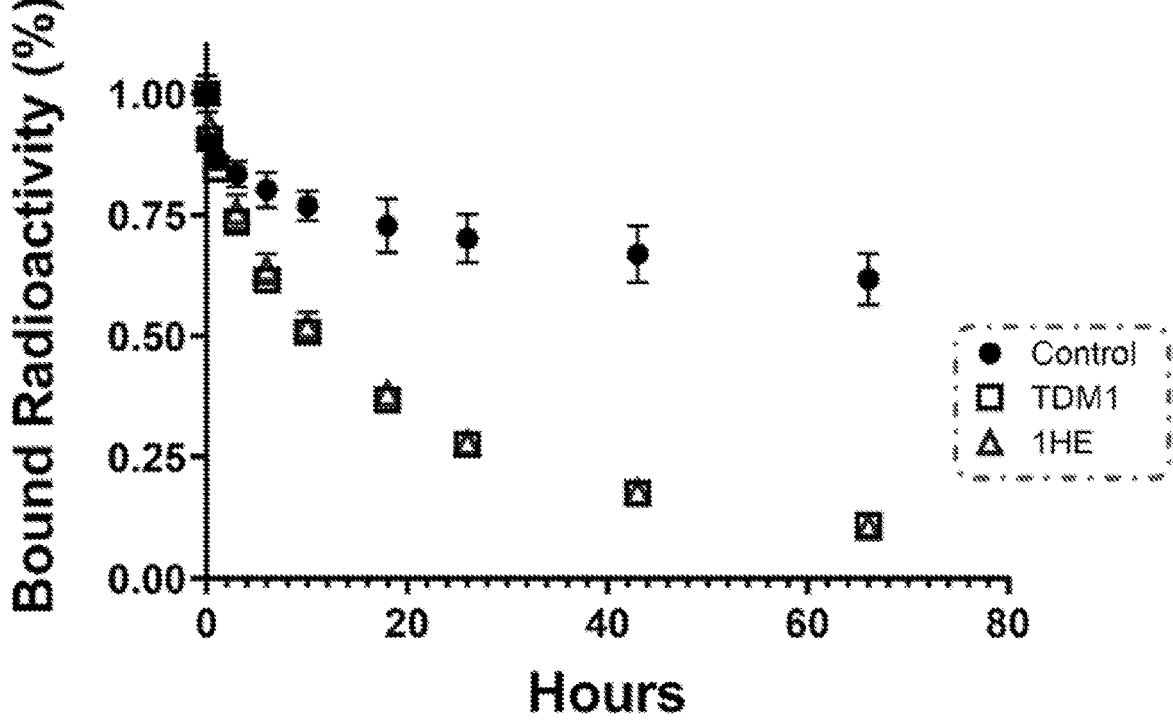
FIG. 9: Radio-tracer 1HE-Trastuzumab dissociation study. Dissociation of 125I-1HE from trastuzumab immobilized magnetic beads. 125I-1HE bound beads were incubated with a 0.1% BSA-PBS control or with 1 μM ado-trastuzumab emtansine (T-DM1), or 1 μM cold-1HE in 0.1% BSA-PBS to prevent rebinding. At the indicated time-points, the supernatant was removed, fresh buffer-solution added, and bound radioactivity assessed. The addition of cold-1HE or free trastuzumab emtansine (T-DM1) led to overlaying dissociation curves, whereas the dissociation rate in blank buffer was significantly slower due to [125]I-1HE rebinding trastuzumab-beads. Individual points represent the mean of triplicate samples with standard deviation error bars.
Figure 10:
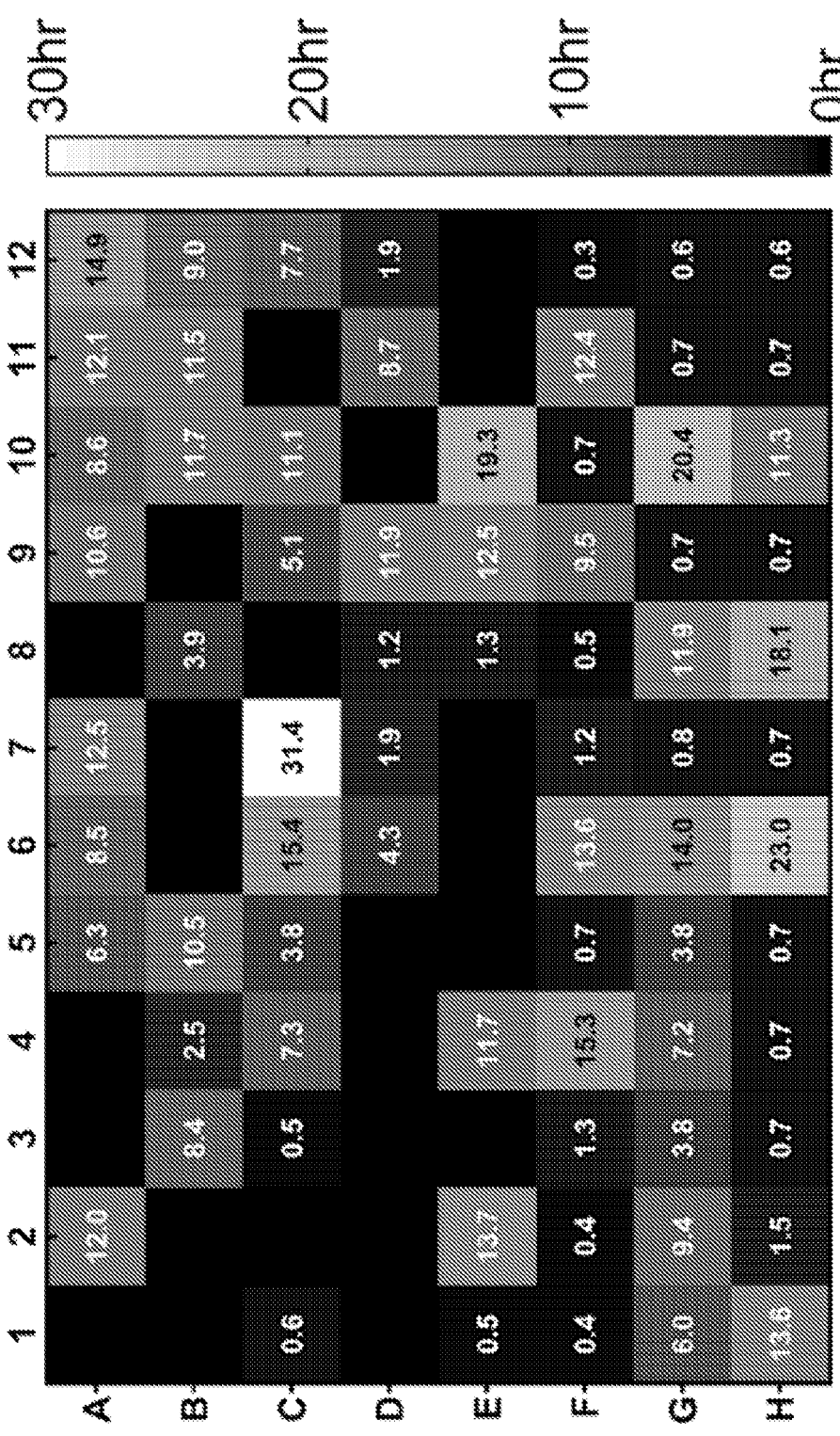
FIG. 10: Representation showing results of low-affinity screening. Estimated half-lives are shown for the 96 colonies screened from the low-affinity panning. Solid black squares represent wells with no binding signal.
Figure 11:
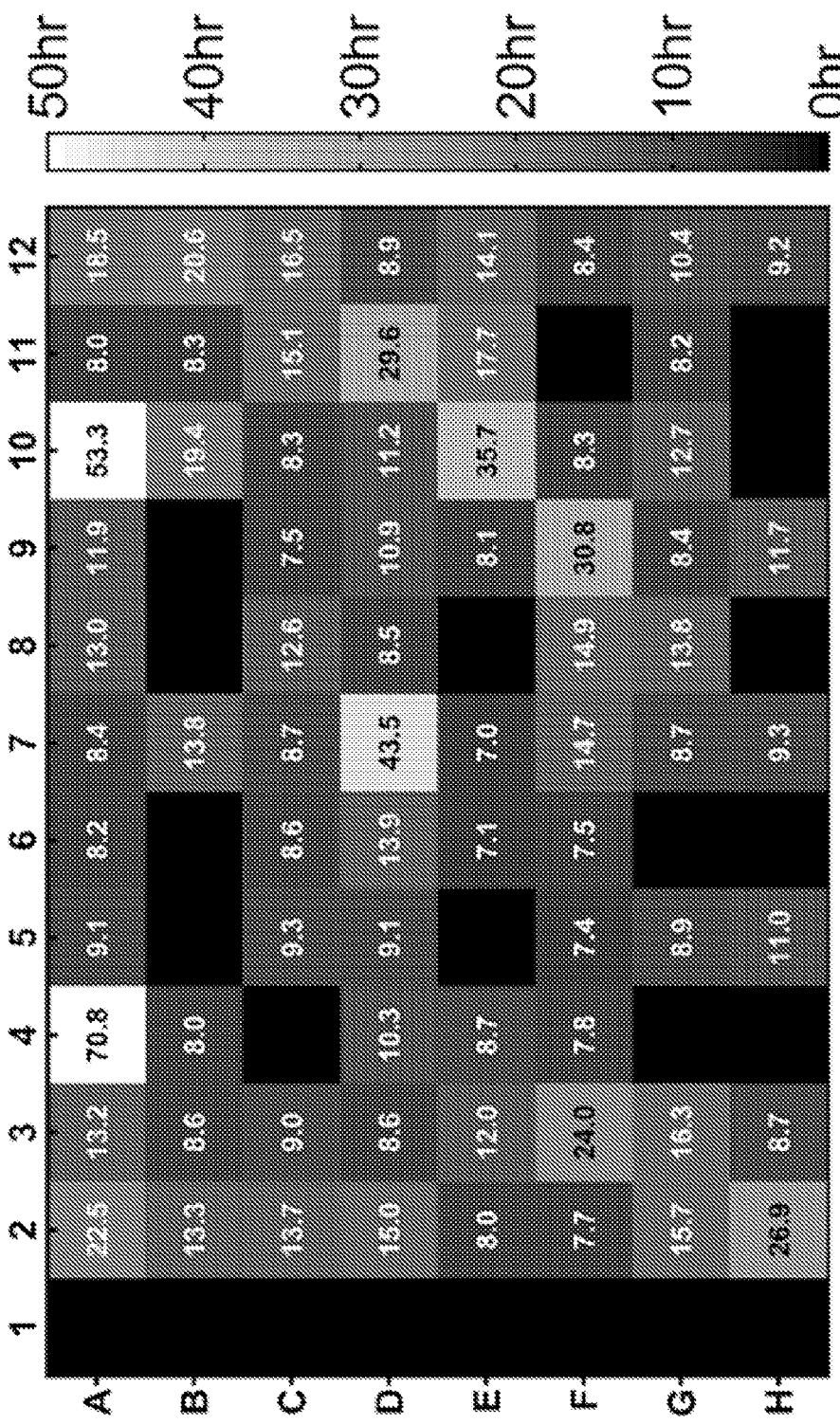
FIG. 11: Representation showing results of high-affinity screening. Estimated half-lives are shown for the 88 colonies that were screened following the high-affinity panning. Column 1 was left blank for control samples. Solid black squares represent wells with no binding signal.

Amine modified dynabeads were covalently coupled with trastuzumab following manufacturers recommendations. 1HE was radiolabeled with $^{125}I$ with a modified chloramine-T procedure. $^{125}I$-1HE with 0.1% BSA/PBS was incubated for 1 hour with trastuzumab modified beads with 3 subsequent washes with 0.1% BSA/PBS. Bound radioactivity was assessed through gamma counting with correction for non-specific absorption using unmodified dynabeads. $^{125}I$-1HE bound Dynabeads were incubated with 0.1% BSA/PBS with and without 1 uM unlabeled 1HE or 1 uM T-DM1 with 3 replicates per group. At the designated timepoints supernatant was removed, radioactivity assessed, and fresh solution added. The 1HE and TDM1 dissociation groups show identical radioactivity loss, with a predicted half-life of 1HE-Trastuzumab binding of 15 hours. 125I-1HE dynabeads incubated with just 0.1% BSA/PBS have a slower rate of radioactivity loss, indicating rebinding of radiolabeled 1HE to immobilized trastuzumab. The unlabeled 1HE or T-DM1 prevent rebinding to trastuzumab immobilized beads through competition for binding (FIG. 9).

The work shown here is the first strategy to bypass the binding site and improve antibody tumor distribution without altering an antibody's native structure or affinity. Transient competitive inhibition is a unique and elegant strategy that can be adapted to any antibody therapeutic directed against solid tumor antigens. As an example, we have demonstrated competitive inhibition can improve trastuzumab distribution in solid tumors and improve T-DM1 efficacy in a mouse xenograft model.

Example 3

This examples describes generation of mutants of 1HE and characterization of the mutants.
Methods
Phage Library Construction One nanogram of 1HE DNA with NdeI and XhoI restriction digestion overhangs was used as the template DNA for error-prone polymerase chain reaction (PCR). PCR primers were designed with sF1 restriction digest overhangs for ligation of the PCR product into the pComb3XSS phagemid plasmid (Addgene, Cambridge, MA, 63890). Error-prone PCR buffer conditions are provided in Table 1. Error-prone PCR product was obtained following 14-cycles of denaturation at 94° C. for 1 minute, annealing at 52° C. for 1 minute, and extension at 68° C. for 3 minutes with a final 10-minute extension. PCR product (1 μg) was ligated into the pComb3XSS phagemid (2 μg) and transfected into TG1 *E. coli* cells (Lucigen, Middleton, WI, 60502) through electroporation. Following electroporation, transformed bacteria were serially diluted up to $10^4$ and spread over lysogeny broth (LB) agar plates supplemented with 2% glucose and 100 μg/ml ampicillin. Remaining transformed bacteria were spread onto four 245 mm square dishes containing LB agar with 2% glucose and 100 ug/ml ampicillin. The next day the library size was determined through colony counting and the bacteria from the 245 mm plates scrapped and inoculated into 8 mLs of LB with 8 mLs of 40% sterile glycerol. The library was stored in aliquots at −80° C.
Phage Isolation An aliquot of the phage library was removed from −80° C. and inoculated into 60 mL of 2×YT medium with 100 μg/ml ampicillin and 2% glucose. The inoculated medium was grown at 37° C. to a 600 nanometer (nm) optical density of 0.4-0.6. Subsequently, 10 mL of the 2×YT culture was transferred to a 50 mL conical and 1 μL of CM13 helper phage (Antibody Design Laboratories, San Diego, CA, PH020L) added with a 1-hour incubation at 37° C. in a shaker incubator. Infected cells were pelleted by centrifugation at 2,800 rotational centrifugal force (RCF) for 10 minutes. Pelleted cells were re-suspended in 50 ml of 2×YT media with 100 μg/mL ampicillin and 50 μg/mL kanamycin and incubated overnight at 30° C. in a shaker incubator. The following day, the culture was centrifuged for 15 minutes at 3,200 RCF to pellet TG1 cells. The media supernatant was decanted into two 50 mL conicals, and 6 mL of 20% (wt/v) PEG6000/2.5 M NaCl solution was added and conicals placed in ice for 30-minutes. Precipitated phage was pelleted by centrifugation at 10,000×g for 20 minutes. Pelleted phage was re-suspended in 1 mL of PBS and centrifuged for 1.5 minutes at 16,000×g in a microcentrifuge to pellet any residual bacteria. Phage concentration was determined prior to panning via a titration method. Briefly, phage was serially diluted by factors of 10 in PBS, and 10 μL of each dilution added to 90 μL of TG1 cells in mid-log phase growth with a subsequent 15-minute incubation at 37° C. Infected TG1 cells from each dilution were spread on LB agar plates with 100 μg/mL ampicillin and 2% glucose and plates incubated overnight at 37° C. Phage concentration was determined by counting colonies on the plate with the highest dilution of phage that grew between 20-200 bacterial colonies.
Panning Trastuzumab was chemically conjugated to Dynabeads following manufacturer recommendations (Thermo Fisher Scientific, Waltham, MA, 14321D). Prior to panning, trastuzumab modified beads were blocked with 2% milk in phosphate buffered saline pH 7.4 (PBS) for one hour. Two panning strategies were used to isolate low- and high-affinity binders, relative to 1HE. For the first round of panning, the phage library was diluted 100-fold $(8.2×10^{11}$ phages/ml) into a 0.2% milk PBS solution and incubated with trastuzumab modified beads for one hour. Following incubation, beads were washed five times for five minutes with PBS. Following washing, a 5 μM solution of 1HE in PBS was added and incubated for two hours. For the low-affinity panning method, the supernatant, following the two-hour incubation with 1HE, was removed, and phages amplified in TG1 cells. The panning was repeated identically, with the amplified phage from the previous round for two additional rounds. For the high-affinity panning strategy, following the two-hour dissociation and supernatant removal, trastuzumab modified beads were incubated with a 100 mM glycine pH 2.0 buffer for ten minutes. Subsequently, the eluate was removed and neutralized with the addition of 75 μl of 1M TRIS-HCL pH 9. The output titer was amplified, and two additional pannings performed with a 24-hour and a 72-hour dissociation, for the $2^{nd}$ and $3^{rd}$ round, respectively, in a PBS buffer with 5 μM 1HE. The final output titer was infected into TG1 cells, incubated at 37° C. for 2 hours, with 50 μg/ml ampicillin added 1 hour into incubation. Subsequently, phage infected TG1 cells were pelleted by centrifugation, lysed, and phage DNA purified using a plasmid purification kit. Purified phage DNA from the high-affinity panning was transformed into the *E. coli* strain BL21DE3 (New England Biolabs, Ipswich, MA, C2527H), serially diluted, spread onto LB agar plates with 100 μg/ml ampicillin, and grown overnight at 37° C. Purified phage DNA from the low-affinity panning was digested with XhoI and NdeI restriction enzymes and separated from the Pcomb3XSS plasmid through agarose gel electrophoresis and purified using a gel extraction and purification kit. Low-affinity mutant DNA was ligated into the expression plasmid pET22b(+) (Millipore-Sigma, Burlington, MA, 69744) and transformed into the *E. coli* strain SHuffle (New England Biolabs, Ipswich, MA, C3029J). Transformed cells were spread onto an LB agar plate with 100 µg/ml ampicillin and grown overnight at 30° C.

Screening

A master plate was established by inoculating single SHuffle or BL21DE3 bacterial colonies into the wells of a 96 well plate with 200 µL of LB medium with 100 ug/ml ampicillin, and 20% glycerol and grown overnight at 30° C. The following day, 20 µl of overnight growth media from each well was inoculated into individual wells of a deep well plate with 1 mL of LB, and the starter plate stored at –80° C. The expression plate was grown in a shaker incubator at 300 rpm at 37° C. for BL21DE3 or 30° C. for SHuffle cells to an optical density at 600 nm of 0.4-0.8. Expression was induced with the addition of 1 mM isopropyl β-d1-thiogalactopyranoside (IPTG) and incubated overnight at 16° C. and 300 rotations per minute (RPM). The next day bacterial cells were pelleted by centrifugation at 3,900 RCF for 15 minutes. Following centrifugation, the culture media was removed, and 100 uL of BugBuster® (Millipore-Sigma, Burlington, MA, 70584) with 10 mg/ml lysozyme, and a 1:1000 dilution of Benzonase® (Millipore-Sigma, Burlington, MA, E1014) was added to each well, and bacterial pellets resuspended by pipetting. Cells were incubated with lysis buffer for 15 minutes at room temperature on a shaker platform at 300 rpm. NUNC Maxisorb plates (Thermo Scientific, Waltham, MA, 439454) were incubated with 250 µL of 4 µg/ml trastuzumab in a 20 mM disodium phosphate buffer (pH unadjusted) overnight. The following day, enzyme linked immunosorbent assay (ELISA) plates were blocked with the addition of 250 µL of a 1% bovine serum albumin (BSA) solution for one hour. The bacterial lysate from the expression plate was diluted 10-fold in a 0.1% BSA solution, and 25 µl added to individual wells of an ELISA plate containing 225 µL of PBS. The plate was incubated with diluted lysate for one hour and then washed four times, with 250 µl of phosphate-buffered 0.05% Tween-20 (wash buffer). For the high-affinity clones, ELISA screening was run in duplicate wells. Following binding, a well for each colony was incubated in PBS, and another well for each colony incubated with 1 µM 1HE to prevent rebinding for 40 hours. After 40 hours, the wells were washed four times with wash buffer and 250 µl of a 1:2,000 dilution of an anti-hemagglutinin alkaline phosphatase (AP) conjugated secondary antibody (Millipore Sigma, Burlington, MA, A5477) in 0.1% BSA PBS added to each well and incubated for one hour on a shaker incubator at 300 RPM. Following incubation, wells were washed three times with wash buffer and two times with distilled water (dH₂O). 250 µl of 4 mg/ml para-nitrophenyl phosphate (PnPP) in a 10 mM diethanolamine pH 9.8 buffer was added to each well, and the change in absorbance at 405 nm monitored using a SpectraMax 340PC plate reader (Molecular Devices, San Jose, CA) for 10 minutes at 30-second intervals. An estimate for the trastuzumab binding half-life for each clone was calculated using the half-life equation using the signal from the PBS well as time=0 and the signal from the well incubated with 1HE as time=40 hours. For the low-affinity panning clones, a similar approach to estimate binding half-life was used. Individual clones were run in triplicate, with a 3-hour and a 6-hour dissociation time point. In addition, 500 µM of trastuzumab was added to block rebinding for the 3- and 6-hour timepoints and a 1:5,000 dilution of an anti-hexahistidine tag AP secondary antibody (Abcam, Cambridge, United Kingdom, ab49746) used for detection.

Sequencing

11 Colonies from the low-affinity panning and 13 colonies from the high-affinity panning were selected for DNA sequencing. Mutants were grown in 10 mL of LB media with 100 µg/ml ampicillin overnight at 37° C. for BL21DE3 cells or 30° C. for SHuffle cells. The next day, cells were pelleted, lysed, and DNA purified using a plasmid purification kit. DNA concentration was determined using a nanodrop and diluted to 100 ng/ml. Low-affinity clones in the Pet22b vector were sequenced using T7 promoter primers, and high-affinity clones were sequenced using pComb3FOR and pComb3REV primers. Sanger sequencing was completed at the Roswell Park sequencing core facility (Buffalo, NY).

Dissociation Rate Screening

1HE mutants were selected from the DNA sequencing results for the characterization of the trastuzumab dissociation rate constant. Individual mutants were expressed and purified using a nickel chromatography resin, as previously described (16). Nunc Immobilizer Amino (Thermo Fisher Scientific, Waltham, MA, 436006) plates were incubated with 100 µL of 5 µg/ml of trastuzumab in a 100 mM disodium phosphate pH 8 buffer overnight. The following day, unreacted sites were blocked with 10 mM ethanolamine in a 100 mM sodium bicarbonate buffer pH 9.5 for one hour. Purified mutants were incubated for one hour and subsequently washed three times with wash buffer. Following washing, 0.1% BSA PBS solution was added to the initial timepoint wells. Dissociation timepoint wells for the low-affinity mutants were incubated in a buffer with 500 nM trastuzumab, and the high-affinity mutants were incubated in a buffer with 1 µM of purified 1HE. At individual time points, the buffer in the time point wells was removed by pipetting, and the wells washed three times with wash buffer and 0.1% BSA PBS added. At the terminal time point, all wells were washed three times with wash buffer, and secondary antibodies added at the dilutions listed above for one hour at room temperature. Following secondary incubation, plates were washed three times with wash buffer and three times with dH₂O. 250 µl of 4 mg/ml PnPP in a 10 mM diethanolamine pH 9.8 buffer was added to each well, and absorbance values read for 10 minutes at 30-second intervals. The change in absorbance per minute for each well was divided by the average change in absorbance per minute for the initial time point wells, and the resulting dissociation curves fit to a monoexponential decay function in GraphPad Prism 7 (GraphPad, San Diego, CA). Each time point was run in triplicate for each mutant.

Results

1HE Mutants

Figure 4:
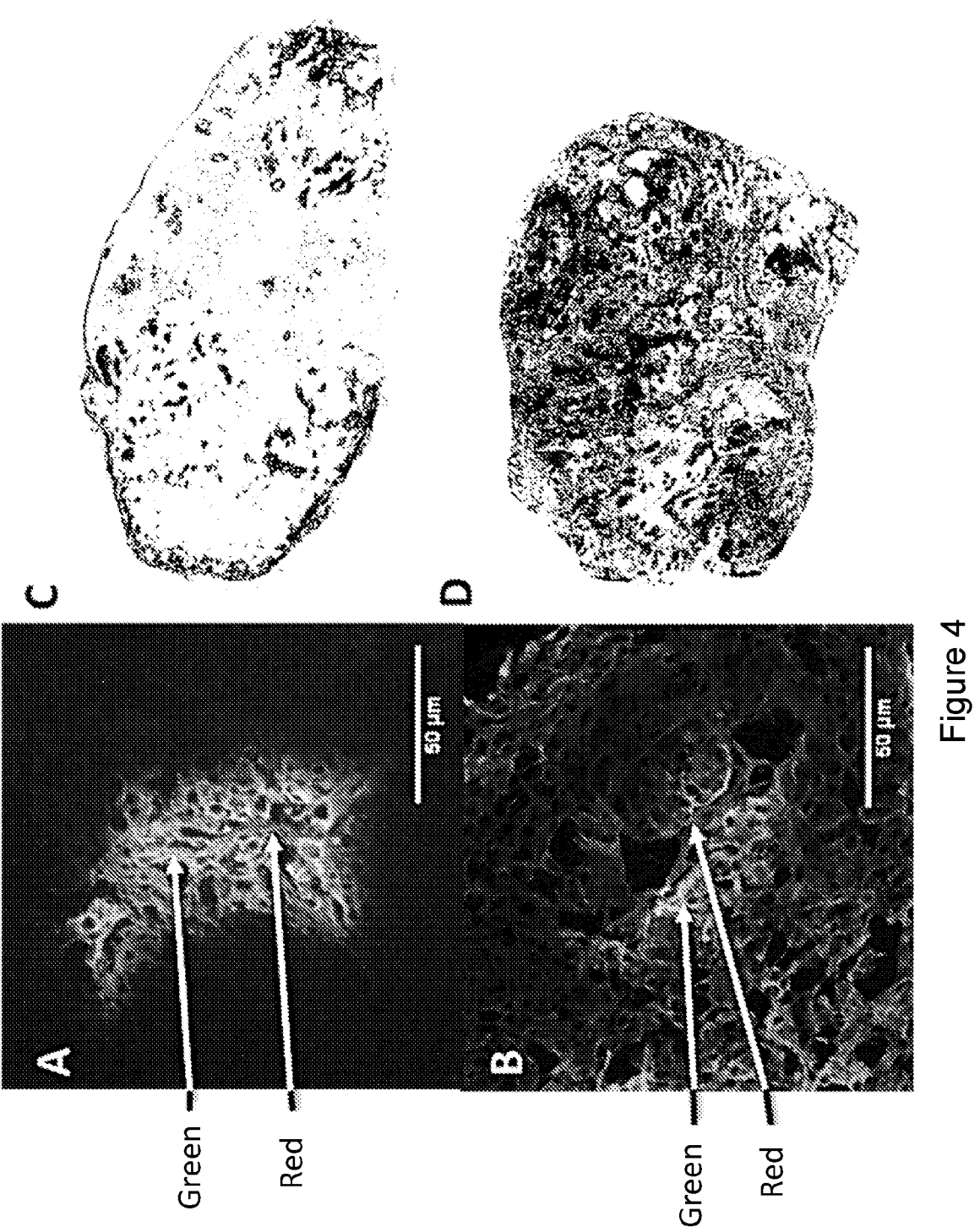
FIG. 4: Trastuzumab tumor distribution with and without 1HE co-administration (A) Trastuzumab administered alone (green) is restricted around vasculature (red) whereas 1HE co-administration increased trastuzumab tumor penetration as indicated by the diffuse staining from the point of extravasation (B). Whole tumor sections of trastuzumab and trastuzumab:1HE are shown in (C) and (D), respectively, images where converted to black and white with regions of trastuzumab positive fluorescent staining 2× greater than background appearing in black. 1HE co-administration increased the tumor exposure to trastuzumab with only a small fraction of the tumor area not staining positive for trastuzumab, in contrast to tumors treated with trastuzumab alone.
Figure 5:
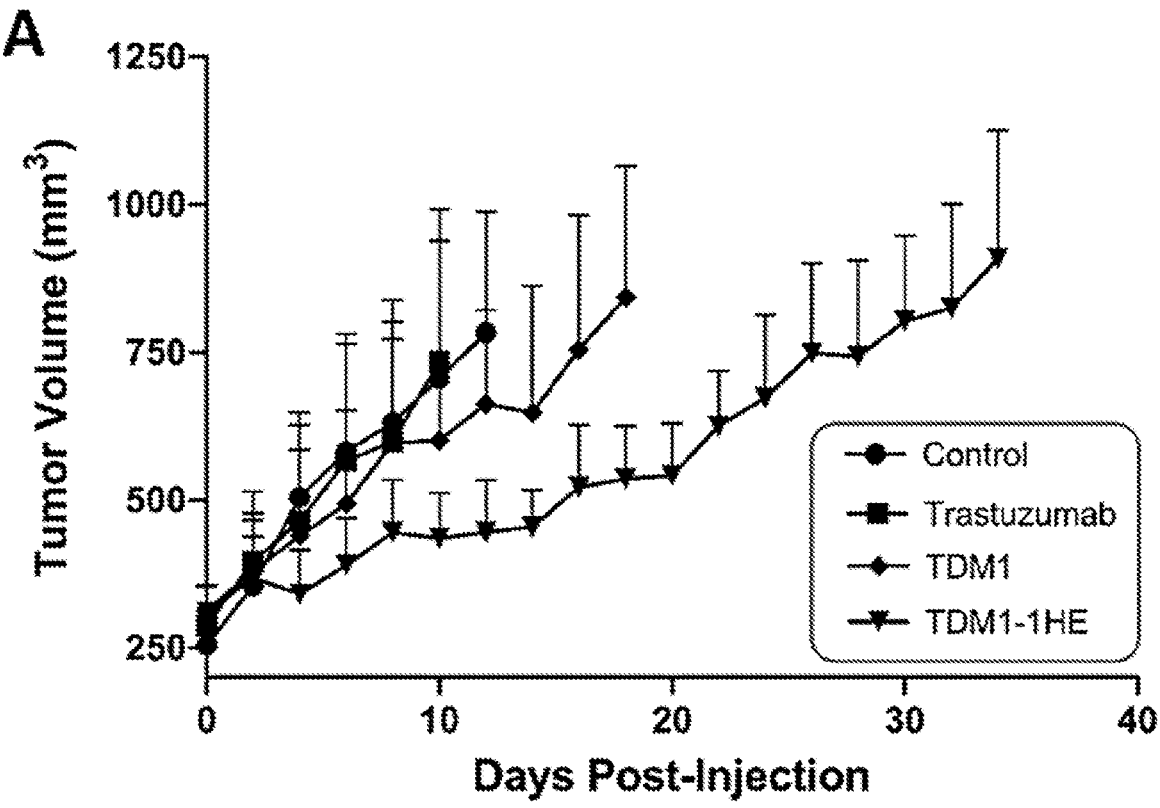
FIG. 5: TDM-1 efficacy with and without 1HE (A) Tumor growth curves for each dose group with curves ending at the first death event (tumor volume greater than 1200 mm³). Tumor volume data represents the group mean with standard deviation error bars. (B) Survival curves shown for each group with statistical significance in survival using the log-rank test set at p≤0.05. Trastuzumab did not significantly extend life-span in comparison to the control group (p=0.68). T-DM1 alone significantly improved survival from the saline group (p=0.033) but not the trastuzumab group (p=0.27). T-DM1 co-administered with 1HE had a significant increase in survival from T-DM1 alone (p=0.0054) and both the trastuzumab (p=0.004) and saline groups (p<0.0001). The saline control and 10 mg/kg trastuzumab dose groups had 7 mice/group, the 1.8 mg/kg T-DM1 and 1.8 mg/kg T-DM1 and co-administered 1HE had 9 mice/group.
Figure 5:
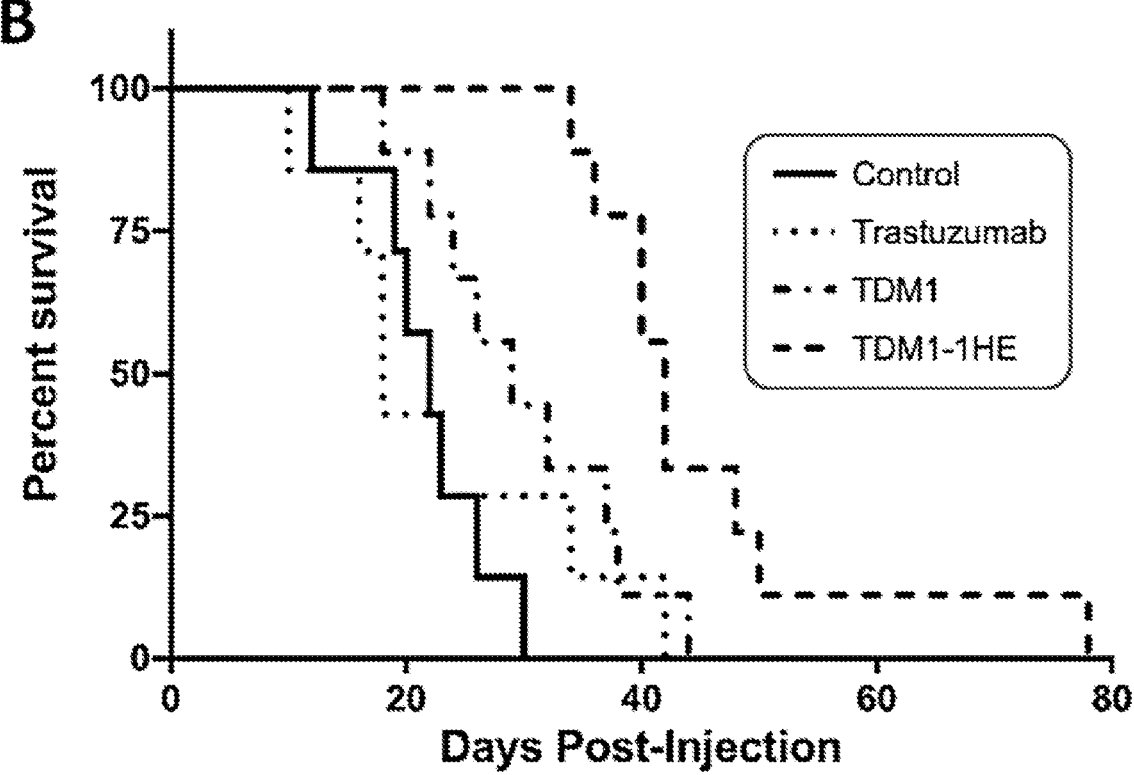

Following panning, 96 colonies from the low-affinity panning and 88 colonies from the high-affinity panning were screened using ELISA to estimate the half-life of trastuzumab binding for each colony. FIG. 1 shows the estimated half-life for each of the low-affinity colonies, and FIG. 2 shows the estimated half-life for the high-affinity colonies. Colonies from individual wells were selected over a range of half-lives from each panning method and DNA sequenced. Amino acid sequences are provided in FIG. 3 with clones from the low-affinity panning starting with the number 1 and high-affinity clones starting with the number 2. All the sequenced colonies had at least one mutation from the parent sequence of 1HE, and all were unique in comparison to the other mutants. Two mutation "hot-spots" can be observed for both the low and high-affinity mutants from the parent DNA. Five of the eleven low-affinity mutants had mutations in the center of complementary determining region two (CDR2), with four having mutations at aspartate 56 (D56). Of the thirteen sequenced colonies from the high-affinity panning, four shared an identical mutation of threonine 103 to alanine (T103A) in CDR3. None of the four colonies with the shared T103A mutations had identical sequences, indicating the mutants originated from different parent phages. An open reading frame shift that resulted in the deletion of amino acids E1-A33, which includes CDR1, is observed for three of the mutants, indicating CDR1 is not involved in trastuzumab binding. Eight low affinity and nine high-affinity mutants were selected to determine the dissociation rate constant from trastuzumab using the covalent ELISA method described in the methods section. Dissociation curves and monoexponential decline fittings for individual clones are shown in FIG. 4. Best-fit dissociation rate constant (koff) values and estimated half-life's of trastuzumab binding is provided in Table 2. 1D6 with a mutation of D56N had the fastest dissociation rate with a trastuzumab binding half-life of 3.9 hours. 2E10 with the mutations L18Q and T103A had the slowest dissociation rate with an estimated binding half-life of 481.6 hours. All clones with a mutation at D56 have a faster koff than 1HE, whereas all mutants with a T103 mutation have a slower koff than 1HE.

Amino Acids Involved in Binding

Although the 1HE mutants identified in the current study span a wide range of dissociation rates constants, additional constructs with specific binding affinities or enhanced stability may be generated based on the present disclosure.

Additional clones with unique sequences and unique trastuzumab binding affinities can be identified by screening further colonies. The sequences that have been identified, and characterized, provide information on the paratopes of 1HE that are responsible for trastuzumab binding. The center of CDR2 appears to be critical for high-affinity binding to trastuzumab, as most of the clones with faster dissociation rates have mutations at [59]NGDST[63]. Alvarez-Rueda et al. reported the CDR2 residues [59]NGDST[63] as being similar to the HER2 motif [571]NGS[573], which is part of a region of HER2 that is bound by trastuzumab. Therefore, 1HE mutants with faster dissociation rate constants may be rationally designed through site-directed-mutagenesis at the [54]NGDST[58] motif of CDR2. Based on the crystal structure of trastuzumab in complex in with HER2, only the A and D residues are likely to interact with trastuzumab. Consistent with the A and D residues being critical for trastuzumab binding, none of the sequenced colonies had mutations at these residues. Threonine 103 was observed to be a common mutation site among the mutants with slower dissociation rate constants, relative to wild-type 1HE. Specifically, six mutants had non-conservative mutations of threonine to alanine, serine, or isoleucine. Identification of these critical mutation "hot-spots" can be used for rational design of competitive inhibitors or allow informed selection of 1HE colonies for further characterization, following DNA sequencing.

While the invention has been described through illustrative examples, routine modifications will be apparent to those skilled in the art, which modifications are intended to be within the scope of the invention.

What is claimed is:

1. A method for inhibiting the growth of a tumor comprising administering to an individual in need of treatment: i) an anti-tumor antibody, alone or conjugated to a cytotoxic agent, and ii) an anti-idiotypic antibody, wherein the anti-idiotypic antibody is directed to the anti-tumor antibody, wherein the anti-tumor antibody is trastuzumab or trastuzumab conjugated to the cytotoxic agent, and wherein the anti-idiotypic antibody comprises a derivative of SEQ ID NO:2, wherein the sequence of the derivative of SEQ ID NO:2 is selected from SEQ ID NO:2 comprising a mutation of the sequence of SEQ ID NO:2 selected from the group of mutations consisting of T103A, L11M, F29L, V32A, K76R, Y111H, N54D, D56G, N74S, Q13H, S85N, T103S, G10D, S31G, D56V, A97V, D56Y, D56N, S57G, a deletion of E1-M34, T103I, D16A, S17G, S631, Y111N, G9D, T28A, T58A, K87E, Q117L, L18Q, V64A, T69S, and a combination thereof.

2. The method of claim 1, wherein i) and ii) are administered as separate compositions.

3. The method of claim 1, wherein i) and ii) are administered in the same composition.

4. The method of claim 1, wherein the cytotoxic agent is a drug, radionuclide, or an immunotherapeutic agent.

5. The method of claim 1, wherein the trastuzumab conjugated to the cytotoxic agent is Ado-trastuzumab emtansine (T-DM1).

6. The method of claim 1, wherein i) is administered intravenously and ii) is administered via a cutaneous route.

7. The method of claim 1, wherein the derivative of SEQ ID NO:2 comprises the T103A mutation.

8. The method of claim 1, wherein the derivative of SEQ ID NO:2 comprises mutations that are one the following:
    a. L11M, F29L, V32A, K76R, and Y111H (1C5); or
    b. N54D, D56G, and N74S (1G1): or
    c. Q13H, S85N, and T103S (1D7); or
    d. G10D, S31G, and D56V (1G11); or
    e. A97V (1C3); or
    f. D56Y (1F3); or
    g. D56N (1D6); or
    h. S57G (1E8), or
    i. a deletion of and E1-M34 and F37Y (1C12); or
    j. T103I (1D12); or
    k. D16A and S17G (1E10); or
    l. a deletion of E1-M34, and S631 and D105E (2H11); or
    m. a deletion of E1-M34, and T103A (2A10); or
    n. Y111N (2G2): or
    o. G9D and T28A (2H2); or
    p. D105E (2F9); or
    q. T58A (2A4); or
    r. K87E (2E11); or
    s. T103A and Q117L (2C4); or
    t. L18Q and T103A (2E10); or
    u. V64A (2G11); or
    v. K76R (2D11); or w. T103A (2D7); or x. T69S (2F3).

\* \* \* \* \*